(12) United States Patent
Botella-Franco et al.

(10) Patent No.: US 12,049,659 B2
(45) Date of Patent: Jul. 30, 2024

(54) PRODUCTION OF ETHANOL AND ENHANCED CO-PRODUCTS USING CO-PRODUCTS AS FEEDSTOCK

(71) Applicant: SHELL OIL COMPANY, Houston, TX (US)

(72) Inventors: Carolina Botella-Franco, The Hague (NL); Sivakumar Sadasivan Vijayakumari, Houston, TX (US); Robert Lawrence Blackbourn, Houston, TX (US); Paul Richard Weider, Houston, TX (US); Ye-Mon Chen, Houston, TX (US); Yi Liang, Houston, TX (US); Daniel Gagne, Houston, TX (US); Ashley Villarreal Baugh, Houston, TX (US)

(73) Assignee: SHELL USA, INC., Houston, TX (US)

( * ) Notice: Subject to any disclaimer, the term of this patent is extended or adjusted under 35 U.S.C. 154(b) by 630 days.

(21) Appl. No.: 17/297,225

(22) PCT Filed: Nov. 26, 2019

(86) PCT No.: PCT/EP2019/082503
§ 371 (c)(1),
(2) Date: May 26, 2021

(87) PCT Pub. No.: WO2020/109268
PCT Pub. Date: Jun. 4, 2020

(65) Prior Publication Data
US 2022/0002762 A1 Jan. 6, 2022

Related U.S. Application Data

(60) Provisional application No. 62/772,719, filed on Nov. 29, 2018.

(51) Int. Cl.
*C12P 7/08* (2006.01)
*C12P 7/10* (2006.01)

(52) U.S. Cl.
CPC ........................... *C12P 7/10* (2013.01)

(58) Field of Classification Search
CPC ................. C12P 7/08; A23K 10/38
See application file for complete search history.

(56) References Cited

U.S. PATENT DOCUMENTS

| | | | |
|---|---|---|---|
| 9,353,332 B2 | 5/2016 | Lewis et al. | |
| 9,428,816 B2* | 8/2016 | Tetarenko | C13K 1/02 |
| 9,624,436 B2* | 4/2017 | Hamilton | C10G 3/50 |
| 9,714,267 B2 | 7/2017 | Emanuele et al. | |
| 2003/0232109 A1* | 12/2003 | Dawley | C08B 30/10 426/53 |
| 2008/0299632 A1 | 12/2008 | Winsness et al. | |
| 2012/0122152 A1 | 5/2012 | Blackbourn et al. | |
| 2016/0237459 A1 | 8/2016 | Brotherson | |

OTHER PUBLICATIONS

Office Action Received for Chinese Application No. 201980075224. X, Mailed on May 4, 2023, 19 Pages (10 Pages of English Translation and 9 Pages of Official Copy).
International Search Report and Written Opinion received for PCT Patent Application No. PCT/EP2019/082503, mailed on Feb. 14, 2019, 10 pages.
Kim et al., "Process Simulation of Modified Dry Grind Ethanol Plant With Recycle of Pretreated and Enzymatically Hydrolyzed Distillers's Grains", Bioresource Technology, vol. 99, Issue No. 12, Nov. 5, 2007, pp. 5177-5192, XP022654838.
Rosentrater et al., "Corn Ethanol Coproducts: Generation, Properties, and Future Prospects", International Sugar Journal, vol. 108, Issue No. 1295, pp. 648-657.
Shurson et al., "The Role of Biofuels Coproducts in Feeding the World Sustainably", Annual Reviews Animal Biosciences, vol. 5, 2016, pp. 229-254.
Moreau et al., "Aqueous Extraction of Corn Oil After Fermentation in the Dry Grind Ethanol Process", Green Veg. Oil Process Revised First Edition., vol. 90, Issue No. 53, 2013, pp. 53-72.

* cited by examiner

*Primary Examiner* — Tekchand Saidha
(74) *Attorney, Agent, or Firm* — SHELL USA, INC.

(57) ABSTRACT

Methods for production of ethanol, distiller's corn oil, and enhanced co-products are disclosed. Methods include obtaining a mixture of one or more co-products of an alcohol production process, which may include wet cake, performing hydrolysis of polysaccharides in the mixture to generate fermentable sugars, fermenting the fermentable sugars in the mixture to produce alcohol, distilling the mixture to remove alcohol from the mixture thereby producing alcohol-containing distillate and enhanced whole stillage, removing released oil from the fermented mixture before distillation and/or from the enhanced whole stillage after distillation, and recovering enhanced wet distiller's grains, enhanced thin stillage, and/or enhanced dried distiller's grains. Compositions disclosed herein include enhanced dried distiller's grains having a crude protein content of at least 45% on a dry weight basis and having a total fat content of less than 10% on a dry weight basis.

12 Claims, 13 Drawing Sheets

PRODUCTION OF ETHANOL AND ENHANCED CO-PRODUCTS USING CO-PRODUCTS AS FEEDSTOCK

CROSS REFERENCE TO RELATED APPLICATIONS

This is a national stage application of International Application No. PCT/EP2019/082503, filed 26 Nov. 2019, which claims benefit of priority to U.S. Provisional application 62/772,719, filed 29 Nov. 2018.

FIELD OF INVENTION

The present invention relates generally to production of ethanol, distiller's corn oil, and enhanced co-products by hydrolysis and fermentation. In particular, it relates to processes that use co-products of ethanol production processes as feedstocks for production of such products.

BACKGROUND OF THE INVENTION

In the US, commercial corn-based ethanol production has been accomplished both by wet milling and dry grinding. The dry grind process has a lower capital investment but suffers from low coproduct value. In the dry grind process, corn is not separated into individual fractions. Instead, the whole corn is processed for 1G ($1^{st}$ Generation) ethanol production. As a result, non-fermentables, such as germ, protein, vitamins, minerals, and fiber are carried through the fermentation process. These non-fermentable co-products are recovered as feedstock for animals, commonly known as dried distiller's grains with solubles (DDGS), which often returns value less than raw corn. In addition to DDGS, distiller's corn oil (DCO) is another key co-product from corn ethanol production. DCO has played a significant role in sustaining the economic viability of the corn industry during periods of weakness in ethanol prices. There exists a need for processes that provide for enhanced recovery of valuable co-products of corn ethanol production such as DDGS and DCO.

The value of DDGS as an animal feed is largely dependent on its protein content. Higher protein content provides greater nutritional benefit for animals. In addition, it is desirable in some circumstances to have a relatively low fat content. While fat in the DDGS enhances the energy density of the feed, high fat content can negatively impact milk production in DDGS-fed cattle and meat texture in DDGS-fed swine. Thus, there also exists a need for processes that enhance the value of DDGS and other co-products of ethanol production processes as an animal feed.

SUMMARY OF THE INVENTION

This disclosure includes compositions and methods that meet the needs identified above. In particular, processes are disclosed that use co-products of ethanol production processes as a feedstock for the production of additional ethanol, DCO, and enhanced co-products. The enhanced co-products have a higher value than conventional co-products due to a higher protein content and reduced fat content, among other properties. The process can also improve the economic performance of the corn ethanol production process, as it increases the total yield of ethanol and DCO from corn feedstock.

In one embodiment, a composition comprising enhanced dried distiller's grains (E-DDG) is disclosed. The composition has a total crude protein content of at least 45% on a dry weight basis and a total fat content of less than 10% on a dry weight basis. In some embodiments, the total protein content of the E-DDG is at least 55% on a dry weight basis. In some embodiments, the total protein content of the E-DDG is at least 60 or 65% on a dry weight basis. In some embodiments, the fiber content of the E-DDG is less than 5% on a dry weight basis. In some embodiments, the starch content of the E-DDG is less than 1% on a dry weight basis. In some embodiments, the starch content of the E-DDG is less than 0.2% on a dry weight basis. In some embodiments, the moisture content of the E-DDG is between 5 and 15% by weight. In some embodiments, the ash content of the E-DDG is less than 2%. In some embodiments, the composition is comprised in an animal feed.

Also disclosed is a composition comprising E-DDG having a total crude protein content of at least 45% on a dry weight basis, a total fat content of less than 10% on a dry weight basis, a fiber content of less than 5% on a dry weight basis, a moisture content between 5 and 15% by weight, and an ash content of less than 2%.

Also disclosed is a method of processing fiber-containing co-products of an alcohol production process, the method comprising: (a) obtaining a mixture comprising one or more of the following co-products of an alcohol production process: (i) wet distiller's grains; (ii) thin stillage; (iii) whole stillage; and (iv) gluten feed; wherein the co-products comprise polysaccharide fibers; (b) contacting the polysaccharide fibers with an α-hydroxysulfonic acid to hydrolyze at least a portion of the polysaccharide fibers, thereby generating fermentable sugars and releasing oil from the polysaccharide fibers; (c) increasing the pH of the mixture by adding a base to the mixture; (d) contacting polysaccharide fibers present in the mixture with enzymes to hydrolyze the polysaccharide fibers, thereby generating additional fermentable sugars; (e) fermenting the fermentable sugars in the mixture to produce alcohol; (f) distilling the mixture to remove alcohol from the mixture, thereby producing an alcohol-containing distillate and enhanced whole stillage; (g) removing released oil from the fermented mixture produced in step (e) and/or from the enhanced whole stillage produced in step f; (h) separating the enhanced whole stillage to produce enhanced wet distiller's grains and enhanced thin stillage; and (i) drying the enhanced wet distiller's grains to remove moisture, thereby producing enhanced dried distiller's grains (E-DDG).

In some embodiments, the alcohol production process that generates the co-products used in step (a) of the method is a process of producing ethanol from dry-milled corn or wet-milled corn. In some embodiments, the mixture of step (a) has a water content of 60 to 90% by weight.

In some embodiments, the α-hydroxysulfonic acid is between 1 and 10% by weight of the mixture in step (b). In some embodiments, step (b) further comprises maintaining the mixture at a temperature between 90° C. and 140° C. In some embodiments, the method further comprises removing at least a portion, preferably at least 70%, of the α-hydroxysulfonic acid from the mixture before step (d). In some embodiments, the removed α-hydroxysulfonic acid is re-used to hydrolyze polysaccharide fibers in another batch of the mixture of step (a).

In some embodiments, the base added in step (c) is magnesium hydroxide, ammonia, slake lime, calcium hydroxide, or potassium hydroxide.

In some embodiments, at least 98% of the fermentable sugar monomers in the mixture are consumed in step (e). In some embodiments, after step (e) the ethanol concentration is at least 30 g/L.

In some embodiments, step (g) further comprises centrifuging the fermented mixture to separate the oil from the fermented mixture, allowing the fermented mixture to sit without agitation to allow the oil to separate from the fermented mixture, centrifuging the enhanced whole stillage to separate the oil from the enhanced whole stillage, allowing the enhanced whole stillage to sit without agitation to allow the oil to separate from the enhanced whole stillage, or a combination thereof. In some embodiments, the weight of the oil removed in step (g) is at least 5% of the total weight of the mixture before removal of the oil.

In some embodiments, the enhanced wet distiller's grains have a moisture content of no more than 70% by weight. In some embodiments, the enhanced thin stillage has a moisture content of 85 to 95% by weight, a crude protein content of at least 60% on a dry weight basis, or any combination thereof. In some embodiments, the method further comprises drying the enhanced thin stillage to produce an enhanced syrup having a moisture content of 50 to 75% by weight and adding the enhanced syrup to the enhanced wet distiller's grains before or during the drying of step (i). In some embodiments, the enhanced thin stillage produced in step (h) is filtered through one or more membranes to produce a protein-enriched rententate with a reduced sulfur content as compared to the enhanced thin stillage. In some embodiments, the protein-enriched retentate is dried to form a protein-enriched enhanced syrup. In some embodiments, the enhanced thin stillage produced in step (h) is mixed with an organic solvent to precipitate proteins in the enhanced thin stillage. In some embodiments, the organic solvent is ethanol, THF, or acetone. In some embodiments, the ratio of solvent to enhanced thin stillage is between 1:1 and 10:1, or is preferably about 3:1. In some embodiments, the precipitate is separated from the supernate and mixed with the enhanced wet distiller's grains produced in step (h) either before or during step (i). In some embodiments, the E-DDG produced in step (i) has: a moisture content of 5 to 15% by weight; a total protein content of at least 60% on a dry weight basis, preferably at least 65% on a dry weight basis; a total fat content of no more than 10% on a dry weight basis; a fiber content of less than 5% on a dry weight basis; a starch content of less than 1% on a dry weight basis; an ash content of less than 2% on a dry weight basis; or a combination thereof.

In some embodiments in which oil is separated from the fermentation broth before distillation is performed, the separation is achieved by a gravity settler, and alternative subsequent processing steps are performed. In such embodiments, the decanted oil is flashed to remove any water and/or ethanol present in the oil, and the water and/or ethanol are recovered and combined with the heavy liquid fraction from the settler and directed to the distillation column. The combined fermentation broth is then distilled, and the enhanced whole stillage from the distillation is directed to a multi-stage evaporator to produce a syrup, which is further dried to produce E-DDGS. In some embodiments, the syrup is dried by spray drying. These processing steps may also be used in any of the other embodiments disclosed herein.

Also disclosed is a method of processing fiber-containing co-products of an alcohol production process, the method comprising: (a) contacting polysaccharide fibers present in a mixture comprising one or more co-products of an alcohol production process with an α-hydroxysulfonic acid to hydrolyze at least a portion of the polysaccharide fibers, thereby generating fermentable sugars and releasing oil from the polysaccharide fibers, wherein the one or more co-products of an alcohol production process comprise one or more of the following: (i) wet distiller's grains; (ii) thin stillage; (iii) whole stillage; and (iv) gluten feed; (b) increasing the pH of the mixture by adding a base to the mixture; (c) contacting polysaccharide fibers in the mixture with enzymes to hydrolyze the polysaccharide fibers, thereby generating additional fermentable sugars and releasing further oil from the polysaccharide fibers, wherein the temperature of the mixture is between 50 and 55° C.; (d) incubating the mixture with yeast under anaerobic conditions to produce alcohol by fermenting fermentable sugars produced in steps (a) and (c), wherein the temperature of the mixture is between 25 and 35° C.; (e) distilling the mixture to remove alcohol from the mixture, thereby producing an alcohol-containing distillate and enhanced whole stillage; (f) removing released oil from the fermented mixture produced in step (d) and/or from the enhanced whole stillage; (g) separating the enhanced whole stillage to produce enhanced wet distiller's grains and enhanced thin stillage; and (h) drying the enhanced wet distiller's grains to remove moisture, thereby producing enhanced dried distiller's grains (E-DDG).

Also disclosed is a method of processing fiber-containing co-products of an alcohol production process, the method comprising: (a) contacting polysaccharide fibers present in a mixture comprising wet distiller's grains with α-hydroxyethane sulfonic acid at a concentration of 2.5 to 3.5% by weight of the mixture, preferably 3% by weight, at a temperature of 130 to 140° C., preferably 135° C., for a duration of at least 50 minutes to hydrolyze at least a portion of the polysaccharide fibers, thereby generating fermentable sugars and releasing oil from the polysaccharide fibers; (b) increasing the pH of the mixture to between 5.0 and 5.5, preferably 5.3, by adding a base to the mixture; (c) contacting polysaccharide fibers in the mixture with enzymes at a concentration of from 4 to 6% on a dry weight basis, preferably 5%, at a temperature between 50 and 55° C., preferably 53° C., to hydrolyze the polysaccharide fibers, thereby generating additional fermentable sugars and releasing further oil from the polysaccharide fibers; (d) incubating the mixture with yeast under anaerobic conditions for at least 24 hours, preferably at least 48 hours, to produce alcohol by fermenting fermentable sugars produced in steps (a) and (c), wherein the temperature of the mixture is between 25 and 35° C., preferably 32° C.; (e) distilling the mixture to remove alcohol from the mixture, thereby producing an alcohol-containing distillate and enhanced whole stillage; (f) removing released oil from the fermented mixture produced in step (d) and/or from the enhanced whole stillage produced in step (e); (g) separating the enhanced whole stillage to produce enhanced wet distiller's grains and enhanced thin stillage; and (h) drying the enhanced wet distiller's grains to reduce the moisture content to between 5 and 15%, thereby producing enhanced dried distiller's grains (E-DDG). The E-DDG produced in step (h) preferably has one or more of the following properties: a total protein content of at least 45% on a dry weight basis, preferably at least 55% on a dry weight basis; a total fat content of no more than 10% on a dry weight basis; a fiber content of less than 5% on a dry weight basis; a starch content of less than 1% on a dry weight basis; and an ash content of less than 2% on a dry weight basis. When wet distiller's grains are used as the feed for step (a), the total protein content of the E-DDG produced in step (h) can be at least 55% or at least 60% on a dry weight basis.

The terms "a" and "an" are defined as one or more unless this disclosure explicitly requires otherwise.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The terms "substantially," "about," and "approximately" are defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the terms "about" and "approximately" may be substituted with "within [a percentage] of" what is specified, where the percentage includes 0.1, 1, 5, and 10 percent.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. For example, the methods of introducing substances into cells disclosed herein can "comprise," "consist essentially of," or "consist of" particular components, compositions, ingredients, etc. disclosed throughout the specification.

Other objects, features and advantages of the present invention will become apparent from the following figures and detailed description. It should be understood, however, that the figures and detailed description, while indicating specific embodiments of the invention, are given by way of illustration only and are not meant to be limiting. Additionally, it is contemplated that changes and modifications within the spirit and scope of the invention will become apparent to those skilled in the art from this detailed description.

The feature or features of one embodiment may be applied to other embodiments, even though not described or illustrated, unless expressly prohibited by this disclosure or the nature of the embodiments. Some details associated with the embodiments described above and others are described below.

DETAILED DESCRIPTION OF ILLUSTRATIVE EMBODIMENTS

Figure 1:
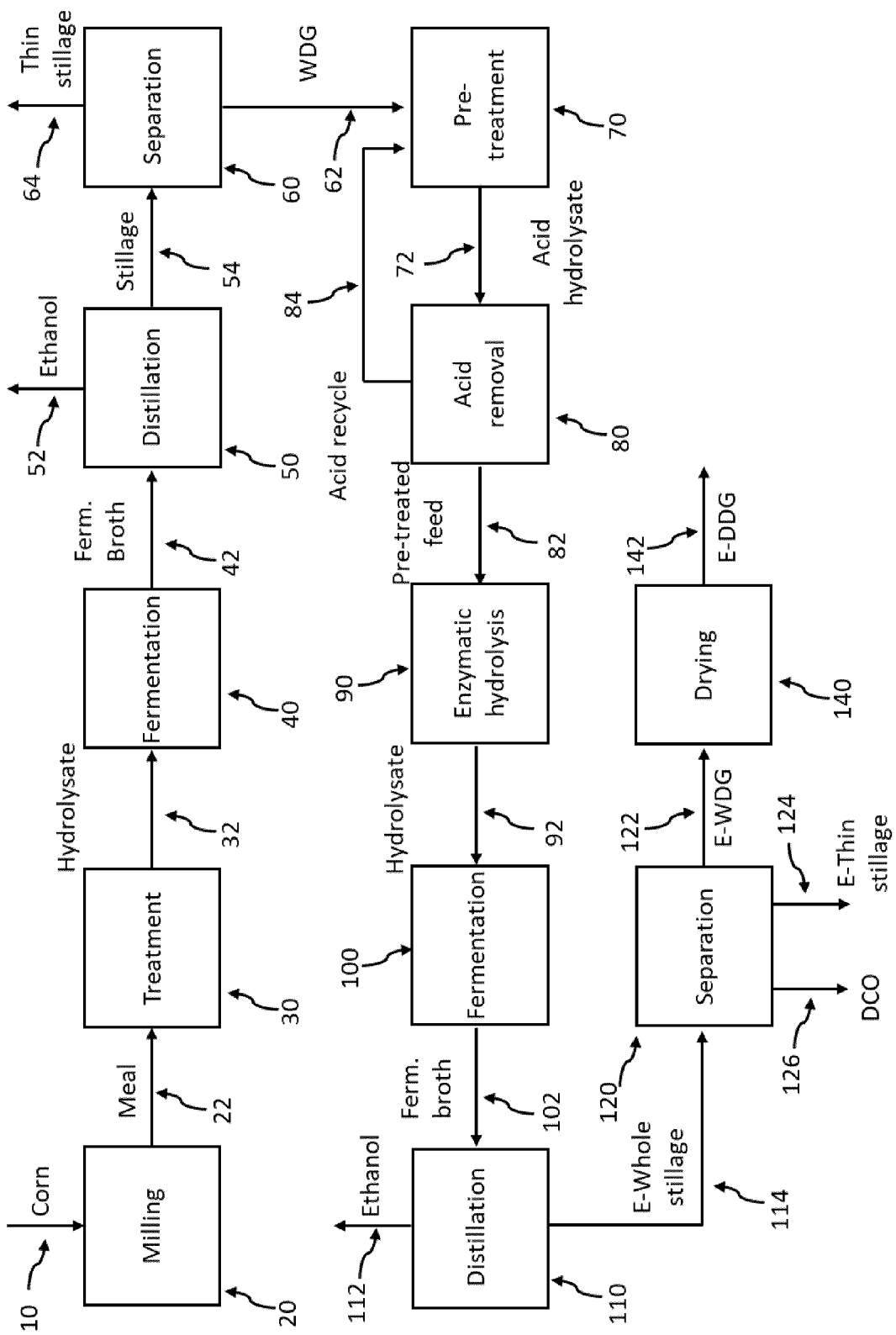
FIG. 1 schematically illustrates a block flow diagram of an embodiment of a treatment process disclosed herein.

A. Overview of Corn Ethanol Production Processes

Embodiments disclosed herein involve production of ethanol and various co-products, such as enhanced dried distiller's grains (E-DDG) and distiller's corn oil (DCO), using as a feedstock wet distiller's grains and/or other co-products of a previously-performed corn ethanol production process. The previous production process can use either dry milling or wet milling of corn as an initial step in corn ethanol production.

In contrast to wet milling, which produces a range of co-products from the various constituents of the corn kernel before ethanol production is carried out, dry milling is focused on converting the starch in whole corn kernels to alcohol and recovering post-fermentation co-products as protein for animal feed. The primary difference between wet and dry milling is in the initial grain processing step. In wet milling, corn is steeped and then separated into its component parts, which are recovered prior to fermentation. In dry milling, the corn is ground into meal and fermented without prior separation of component parts.

In the first step of a typical dry milling process, the corn is hammer-milled and ground to a fine powder called meal. Corn meal is mixed with water, which can be derived from corn grains, makeup water, recycled water, water condensate from evaporators, and/or $CO_2$ scrubber water, producing corn mash. α-amylase is added to the slurry mixer to start the degradation of starch to dextrin. Corn slurry is then cooked using a hydro-heater. Steam enters the cooking system to heat the slurry and a pressure drop is applied to facilitate the mechanical shearing of starch molecules. The slurry is then heated under pressure, which further breaks down fiber and reduce the bacterial levels in the corn mash (K. A. Rosentrater & K. Muthukumarappan, *Int. Sugar J.*, 108:648-57 (2006)).

The cooked mash is liquefied, which partially converts the gelatinized starch to soluble dextrin, decreasing the viscosity significantly. Additional α-amylase is added to this step since the cooking process denatures most of the previously-added enzymes. The yeast propagation process starts aerobically to induce cell growth in the yeast tank. Simultaneously, the fermentation tanks are filled with liquefied mash, and gluco-amylase is added to the process to bring the process of saccharification, i.e., to hydrolyze dextrin to fermentable sugars. When the propagated yeast is ready, it is added to the fermenter and during this step, yeast ferments glucose to ethanol and $CO_2$. A typical corn-to-ethanol plant has three or more fermenters operating in a batch mode in staggered cycles. This anaerobic process is operated at temperatures ranging usually from 30 to 35° C. since higher temperatures can decrease the yeast metabolic activity. $CO_2$ from the process is removed through scrubbers. The fermented mash, known as "beer," may contain approximately 16 v % of ethanol along with non-fermentable solids from the corn and yeast cells. The beer is pumped into continuous distillation columns, where ethanol is separated from the solids and most of the water as an azeotrope. The first distillation columns produce ethanol in concentrations normally ranging from 60 to 80 v %, and water from this process is usually recycled to the α-amylase tank. The ethanol-water mixture is distilled up to the 95.6% azeotropic-concentration point on the second column, where it is sent to a molecular-sieve TSA system, producing anhydrous ethanol.

In a typical dry-mill plant, co-product recovery starts with post-processing of the bottom fraction of ethanol distillation from the fermented mash, which is referred to as "whole-stillage." Whole stillage typically contains 6-16% of total solids, and is a hot, mildly acidic, and viscous fluid, with limited shelf life. Whole stillage is usually dried for easier handling, storage, and end use. The most common practice to handle whole stillage is to transform it into a stable product using a series of unit operations, first using a centrifuge for the solid-liquid separation. The solid fraction from this separation is known as "wet distiller's grains" (WDG) or commonly "wet-cake," and the liquid fraction, which typically contains about 90-95% of moisture, is referred to as "thin stillage." Thin stillage is typically dried to a moisture content of 50-75% to produce "condensed distiller's solubles" (CDS), or commonly "syrup." A portion of the syrup is often combined with wet-cake to produce a nutrient-rich material, which is dried in order to produce "dried distiller's grains with solubles" (DDGS) (G. C. Shurson, *Ann. Rev. Anim. Biosci.*, 5:229-54 (2016)).

A significant portion of thin stillage can be "back-set" as the source of water and nutrients to the cooking step, which yields water and thermal energy savings. This backsetting is often coupled with a series of anaerobic digesters. Thin stillage by itself has been recognized as an excellent energy and protein source for several different animals, such as growing and lactating cattle. It is therefore fed to animals in combination with poor quality feeds, where it acts as an energy and protein supplement. In well balanced diets, thin stillage can improve feed efficiency by reducing dry matter intake.

In addition to DDGS, distiller's corn oil (DCO) is another key co-product that has played a significant role in sustaining the economic viability of the industry during periods of weakness in ethanol prices. DCO is different from the crude corn oil that is obtained from the corn wet milling process. Crude corn oil is marketed for food grade corn oil, and DCO is targeted for biodiesel and animal feed purposes. DCO can be extracted from thin stillage. The energy required to create this DCO is shown to be much lower than that of a wet-mill plant, as it is done post-fermentation and is expected to require much less capital and lower operating costs due to the fermentation conditions applied, thus allowing it to be a viable feedstock for biodiesel production. DCO recovery in dry-mill ethanol plants is usually accomplished by placing the separation step within the thin stillage evaporators. Thin stillage is sent to a first evaporator, DCO is recovered, and then defatted thin stillage is further concentrated to syrup. The utilization of separation aids, such as precipitated and hydrophobic silica, has been described as a further alternative to decrease the need for additional separation units, which can be added on the inlet or outlet of an evaporator (U.S. Pat. No. 9,353,332). The recovery of oil from thin stillage after evaporation using a disk stack centrifuge has also been disclosed (U.S. patent application Ser. No. 12/130, 399). This process includes heating the thin stillage at a temperature >100° C. at a pressure greater than its vapor pressure, followed by a cooling phase which helps to separate the oil from thin stillage. Continuous centrifuges, three-phase decanter centrifuges, and disk stack centrifuges can be used to separate DCO; disk stack centrifuges are particularly suited to removing bound and emulsified oil (R. A. Moreau et al., *Green Veg. Oil Process. Revis. First Ed.*, 90:53 (2013)).

While a high oil content in DDG increases the energy density of DDG for feeding livestock, it can also negatively impact milk production by dairy cattle and texture of pork in DDG-fed swine. Therefore, DDG with reduced fat content, which can be produced using methods disclosed herein, can improve the quality of animal feed. This can be accomplished by liberating and recovering oil present in the fibers of conventional DDG. This has the advantage of reducing the fat content in E-DDG, as well as producing additional DCO.

B. Production of Ethanol and Enhanced Co-Products Using Co-Products of 1G Corn Ethanol Production as Feedstocks A 1G ethanol facility produces bioethanol by fermenting sugars formed from easily hydrolysable starch in corn, as described above. Embodiments of the methods disclosed herein take advantage of the cellulosic sugars hidden in the corn kernel fiber for production of cellulosic ethanol and enhanced co-products, such as E-DDG. Corn kernels consist mainly of starch, but they also contain 10-12% fiber, as well as some protein and fat. The fiber consists of cell walls that contain cellulose and hemicellulose, together with a small amount of lignin. It also contains some starch. The corn kernel fiber is present in co-products of 1G corn ethanol processes such as whole stillage, wet distiller's grains, and dried distiller's grains. To produce cellulosic ethanol from the fiber present in such co-products, cellulose and hemi-celluloses must be broken down into fermentable sugars. The primary obstacle to the usage of the fiber in the wet cake is an expensive "pretreatment" step to release these sugars and make the cellulose and other polysaccharides in the feedstock accessible to enzymatic hydrolysis. One potential pretreatment strategy is dilute mineral acid hydrolysis. The conditions of a successful pretreatment in dilute acid hydrolysis are determined by a combination of three factors: time, temperature, and acid concentration. Increased temperatures increase the rate of breakdown of fibers and release of cellulose, but also result in increased loss of sugars and proteins to degradation products and fouling. Also, increasing acid concentration (to allow for lower temperature) comes at the expense of the acid employed and neutralized salts in downstream equipment. An effective solution to this dilemma is provided by the use of reversible α-hydroxysulfonic acids for pre-treatment, as described in U.S. Pat. No. 9,428,816, which is hereby incorporated into this application by reference. This pretreatment is effective at relatively low temperatures, for example, about 110 to 130° C., and the α-hydroxysulfonic acids are reversible and can readily be removed from the pretreatment slurry and recycled.

α-Hydroxysulfonic acids appear to be as strong as, if not stronger than, HCl since an aqueous solution of the adduct has been reported to react with NaCl, freeing the weaker acid, HCl. The reversible acid can generally be prepared by reacting at least one carbonyl compound or precursor of carbonyl compound with sulfur dioxide and water. For, instance acetaldehyde will react with sulfur dioxide to make α-hydroxyethane sulfonic acid (HESA) according to the following equation:

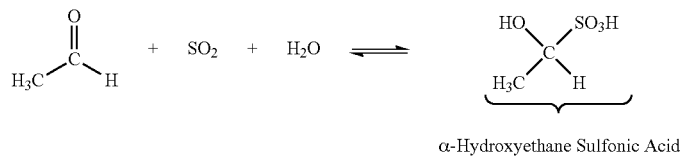

α-Hydroxyethane Sulfonic Acid

As can be seen, the equilibrium can be fully shifted to the feed components by increasing temperature and/or reducing the pressure to drive the $SO_2$ off. Like in this case of acetaldehyde, if the carbonyl is volatile, it is also easily removed into the vapor phase. The acid is hence reversible to readily removable and recyclable materials, unlike mineral acids such as sulfuric, phosphoric, or hydrochloric acid. Methods disclosed herein can use α-hydroxysulfonic acids for pretreatment of feedstocks according to methods described in U.S. Pat. No. 9,428,816.

FIG. 1 illustrates a non-limiting example of a method of producing ethanol, distiller's corn oil, and enhanced co-products from a feed comprising wet distiller's grains. In the illustrated embodiment, corn 10 is subjected to milling 20 to produce meal 22. The meal 22 is then treated 30 to produce a hydrolysate 32 containing fermentable sugars. In a typical treatment step, the meal is mixed with water and the starch is converted into sugars by reaction with enzymes in numerous possible configurations known to those in the art and described in, for example, W. M. Ingledrew et al., The Alcohol Textbook, Fifth Ed., Nottingham University Press, 2009. In a typical ethanol production process, two main enzymes assist in the catalytic breakdown of the starch to glucose. The first is the endoenzyme α-amylase, which acts to break the α-1,4 glycosidic linkage of the starch to produce oligosaccharides of varying molecular weights called "dextrins." The breakdown of dextrins is usually performed in the fermenter using a second enzyme, amyloglucosidase, which hydrolyses the dextrins to glucose monomers, which are fermentable sugars. In one embodiment, the treatment process involves cooking/liquefaction with a slurry tank where ground grain is mixed with water and hydrolyzed in the presence of enzymes to produce fermentable sugars such as glucose. The process may involve cooking or, depending on the enzyme, cold-cook, where the hydrolysis is conducted at fermentation temperature, or no-cook, where enzyme is stirred below the gelatinization temperature of the starch. This treatment step may be conducted in batch, continuous, or semi-continuous processes.

Yeast is added to the hydrolysate 32 to convert the fermentable sugars to ethanol and carbon dioxide in a first fermentation process 40, thereby producing a first fermentation broth 42 containing about 15% ethanol, water, and solids from the grain. The fermentation broth 42 is then distilled in a first distillation process 50, producing an ethanol solution 52 and whole stillage 54. The whole stillage is then separated 60 into thin stillage 64 and wet distiller's grains (WDG) 62. Separation 60 can be accomplished, for example, by decanting, centrifugation, or any other method that can conveniently separate liquid from solids. A portion of the thin stillage can be routed back to the cooking process as makeup water (not shown), reducing the amount of fresh water required by the cook process. The thin stillage can also be concentrated to produce condensed distiller's solubles (not shown).

The wet distiller's grains 62, which may be mixed with thin stillage, whole stillage, or condensed distiller's grains, is then introduced into an acid hydrolysis pretreatment reaction 70 to produce acid hydrolysate 72 in which cellulose fibers, hemicellulose, and starch are released from corn fiber in the wet distiller's grains 62 and made more accessible to enzymatic hydrolysis. The acid hydrolysis reaction 70 may comprise a number of components, including α-hydroxysulfonic acid. The acid hydrolysate 72 (pre-treated feedstock) is then subjected to an acid removal process 80 where the acid is removed in its component form and is recovered (and optionally scrubbed) either as components or in its recombined from and recycled via recycle stream 84 to acid hydrolysis pretreatment reaction 70. The pre-treated feedstock 82 with acid removed is then subjected to enzymatic hydrolysis 90, producing a hydrolysate 92 containing fermentable sugars. Yeast is added to the hydrolysate 92 to convert the fermentable sugars to ethanol and carbon dioxide in a second fermentation process 100, thereby producing a second fermentation broth 102 containing about 15% ethanol, water, and solids from the grain. The fermentation broth 102 is then distilled in a second distillation process 110, producing an ethanol solution 112 and enhanced whole stillage 114. The enhanced whole stillage 114 is then separated 120 into enhanced thin stillage 124 and enhanced wet distiller's grains (E-WDG) 122. The enhanced wet distiller's grains are then dried 140 to produce enhanced dried distiller's grains (E-DDG). The enhanced thin stillage 124 can be concentrated, such as by evaporation under vacuum, to produce enhanced condensed distiller's solubles (E-syrup), which may be mixed with E-DDG 142 to produce enhanced dried distiller's grains with solubles (E-DDGS) (not shown). The separation process 124 can also produce separated distiller's corn oil (DCO) 126 from the whole stillage. For example, a tricanter centrifuge can be used to separate liquids, solids, and fats to produce enhanced thin stillage 124, enhanced wet distiller's grains 122, and DCO 126.

Additional optional processing steps for removal of sulfur may be performed on the E-thin stillage 124 after separation 120. This can be accomplished by membrane separation and/or protein precipitation. A membrane separation process involves passing the E-thin stillage 124 through a membrane or series of membranes having pore sizes ranging from 0.2 to 100 KDa. This produces a retentate that is enriched in protein and low in sulfur, and a permeate stream that is relatively low in protein and high in sulfur. The protein-rich retentate stream can then be further dried, preferably in a spray dryer to produce E-syrup with low sulfur content. A protein precipitation process for removing sulfur involves adding solvents such as ethanol, THF, or acetone to E-thin stillage 124 (or, optionally, to E-syrup) at solvent-to-feed ratios ranging from 1 to 10, and preferably of about 3. The protein-rich, low-sulfur precipitate may be separated from the relatively high-sulfur supernate by filtration or centrifugation and then combined with E-WDG 122.

Some embodiments of the methods disclosed herein do not include the initial processing steps of milling 20, treatment 30, fermentation 40, distillation 50, and separation 60. Instead, some embodiments start with acid hydrolysis 70 of feedstocks produced previously at the same plant or a different plant. Such feedstock can be wet distiller's grains, whole stillage, or thin stillage produced in a corn ethanol plant, or mixtures thereof. The feedstock for production of ethanol and enhanced co-products may also include wet or dry gluten feed made in a wet milling process. The wet milling production process for gluten feed, which is used as a feedstock in some embodiments disclosed herein, is as follows: First, whole corn kernels are soaked in acid. The resulting steep liquor contains protein, minerals, vitamins, and energy sources. The starch and oil are extracted from the swollen kernel. The remaining fiber or bran is mixed with the steep liquor, making wet gluten feed, which in some embodiments may contain about 30 to 50% dry matter. Dry gluten feed is made by drying wet gluten feed, and in some embodiments may contain approximately 90% dry matter. The feedstock for methods disclosed herein may include any combination of wet distiller's grains, whole stillage, thin stillage, and wet or dry gluten. The feedstock may include only one of these substances, or may contain a mixture of 2, 3, 4, or 5 of these substances. In some embodiments, one or more of these substances is excluded from the feedstock. In some embodiments, the feedstock mixture has a water content of at least about, at most about, or about 30, 35, 40, 45, 50, 55, 60, 65, 70, 75, 80, 85, 90, or 95%, or between any two of these values.

Some embodiments of ethanol production methods include contacting polysaccharide fibers present in a feedstock with α-hydroxysulfonic acid to hydrolyze at least a portion of the polysaccharide fibers, thereby generating fermentable sugars and releasing oil from the polysaccharide fibers. This may be accomplished by mixing the feedstock with an α-hydroxysulfonic acid solution, such as by impregnating the feedstock with α-hydroxysulfonic acid using an impregnator. In some embodiments, during an acid hydrolysis pretreatment step, the concentration of α-hydroxysulfonic acid in the mixture with the feedstock is at least about, at most about, or about, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0% by weight, preferably 2.5 to 3.5% by weight of the mixture. The temperature during this acid hydrolysis step may be maintained at least about, at most about, or about 90, 95, 100, 105, 110, 115, 120, 125, 130, 135, or 140° C. for a period of time, preferably 130 to 140° C. In some embodiments, said period of time is about 0.5, 1.0, 1.5, 2.0, 2.5, 3.0, 3.5, 4.0, 4.5, or 5.0 hours, or between any two of these values. The pH during this acid hydrolysis step may be at least about, at most about, or about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0, or between any two of these values. In some embodiments, at least a portion of the α-hydroxysulfonic acid is removed from the mixture with the feedstock. In some embodiments, at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90% of the α-hydroxysulfonic acid is removed from the mixture, or any range derivable therein. Removal may be performed, for example, as described in U.S. Pat. No. 9,428,816. The removed α-hydroxysulfonic acid may be re-used to perform acid hydrolysis of another portion or another batch of feedstock.

In some embodiments, the pH of the mixture after acid hydrolysis is performed is increased by the addition of a base. The base may be, for example, magnesium hydroxide, ammonia, slake lime, calcium hydroxide, or potassium hydroxide, or any combination thereof. In some embodiments, the pH is increased by adding a 14% $NH_4OH$ solution. In some embodiments, the pH is adjusted to at least about, at most about, or about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0, or between any two of these values, preferably between 5 to 5.5. The target pH may be determined by the optimal conditions for enzymatic hydrolysis of polysaccharides and oligosaccharides in the pretreated feedstock. In some embodiments, the pH is maintained at the target pH during enzymatic hydrolysis via periodic addition of base.

In some embodiments, the polysaccharides are further hydrolyzed by enzymes such as cellulases, hemicellulases, and/or pectinases to generate additional fermentable sugars and release further oil from pretreated polysaccharides. In embodiments in which enzymatic hydrolysis is performed, it may be performed as a separate step after acid hydrolysis and before fermentation. In some embodiments, enzymatic hydrolysis is performed for at least a portion of the time during which fermentation is being performed. In some embodiments, enzymatic hydrolysis is performed for a time before fermentation begins and continues for at time after fermentation begins. In some embodiments, the temperature and/or pH may be adjusted at the beginning of fermentation. This may be done, for example, because the optimal conditions for enzymatic hydrolysis may differ from optimal conditions for fermentation. In some embodiments, enzymatic hydrolysis is carried out at a temperature of about 40, 41, 42, 43, 44, 45, 46, 47, 48, 49, 50, 51, 52, 53, 54, 55, 56, 57, 58, 59, or 60° C., or between any two of these values, before fermentation begins, and at a temperature of about 25, 26, 27, 28, 29, 30, 31, 32, 33, 34, 35, 36, 37, 38, 39, or 40° C. after fermentation begins. In some embodiments, the pH is adjusted to 5.0, 5.1, 5.2, 5.3, 5.4, 5.5, 5.6, 5.7, 5.8, 5.9, 6.0, 6.1, 6.2, 6.3, 6.4, or 6.5, or between any two of these values, for fermentation. In some embodiments, acid hydrolysis produces glucose to a concentration of at least about or about 5, 6, 7, 8, 9, 10, 11, 12, 13, 14, or 15 g/L, or between any two of these values. In some embodiments, enzymatic hydrolysis produces glucose to a concentration of at least about or about 10, 11, 12, 13, 14, 15, 16, 17, 18, 19, 20, 21, 22, 23, 24, 25, 26, 27, 28, 29, 30, 31, 32, 33, 34, or 35 g/L, or between any two of these values.

Fermentation of the fermentable sugars to produce ethanol can be accomplished by a variety of microorganisms. For example, the fermentation may be accomplished by *Saccharomyces cerevisiae, Saccharomyces uvarum, Saccharomyces carlsbergensis, Saccharomyces chevalieri, Candida krusei, Candida guilliermondii Candida tropicalis, Candida diddensiae, Candida fabianii, Candida intermedia, Candida maltosa, Candida santamariae, Candida colliculosa, Pichia membranaefaciens, Cryptococcus kuetzingii, Hansenula polymorpha, Kloeckera corticis, Rhodotorula pallida, Rhodotorula rubra, Rhodotorula minuta, Torulopsis norvegica,* or *Trichosporon cutaneum,* or any combination thereof. In some embodiments, the microorganism is capable of fermenting five-carbon sugars such as xylose and arabinose.

In some embodiments, fermentation is carried out at about 25, 26, 27, 28, 29, 30, 31, 32, 33, 34, 35, 36, 37, 38, 39, or 40° C., or between any two of these values, preferably 25 to 35° C. In some embodiments, fermentation is carried out at a pH of 5.0, 5.1, 5.2, 5.3, 5.4, 5.5, 5.6, 5.7, 5.8, 5.9, 6.0, 6.1, 6.2, 6.3, 6.4, or 6.5, or between any two of these values, preferably 5 to 5.5. In some embodiments, fermentation is carried out for a duration of 6, 12, 18, 24, 30, 36, 42, 48, 54, 60, 66, or 72 hours, or between any two of these values, preferably at least 24 hours. In some embodiments, the fermentation consumes at least about 90, 91, 92, 93, 94, 95, 96, 98, 98, 99, or 99.9% of the fermentable sugars present in the mixture after hydrolysis is complete, or between any two of these values. In some embodiments, the fermentation consumes at least about 90, 91, 92, 93, 94, 95, 96, 98, 98, 99, or 99.9% of the glucose present in the mixture after hydrolysis is complete, or between any two of these values. In some embodiments, fermentation produces ethanol in the fermentation broth at a concentration of at least about or about 15, 16, 17, 18, 19, 20, 21, 22, 23, 24, 25, 26, 27, 28, 29, 30, 31, 32, 33, 34, 35, 36, 37, 38, 39, or 40 g/L, or between any two of these values.

Some embodiments include a step of removing oil from the fermentation broth after fermentation but before distillation or from the enhanced whole stillage after distillation. Embodiments can include removing oil at either or both of these times. Oil separation can be accomplished, for example, by centrifugation, by a gravity settler, or by allowing the fermentation broth or whole stillage to sit without agitation. In some embodiments, the weight of the oil removed in this step is at least about 1, 2, 3, 4, 5, 6, 7, 8, 9, or 10% of the total weight of the enhanced whole stillage before removal of the oil.

In embodiments in which oil is removed from the fermentation broth before distillation, the removed oil may be flashed to remove any water or ethanol, which can be recovered and combined with the heavy liquid fraction from the settler for subsequent distillation. The enhanced whole stillage produced by the distillation can then be directed to a multi-stage evaporator to produce a syrup, which can then be dried in a spray dryer to produce E-DDG.

Some embodiments of the enhanced co-products produced according to methods disclosed herein have enhanced qualities for uses such as animal feed. As used herein, "enhanced" co-products, such as enhanced whole stillage (E-whole stillage), enhanced thin stillage (E-thin stillage), enhanced condensed distiller's solubles (E-CDS or E-syrup), enhanced wet distiller's grains (E-WDG), enhanced dried distiller's grains (E-DDG), and enhanced dried distiller's grains with solubles (E-DDGS), are products of a process of treating co-products of a previously performed ethanol production process. As used herein, enhanced dried distiller's grains with solubles (E-DDGS) refers to a mixture of E-DDG and E-CDS that is dried to a desired moisture content.

Some embodiments of enhanced co-products have a higher percentage of protein than conventional co-products, which can make the enhanced co-products a better source of nutrition than conventional co-products. In some embodiments, the enhanced co-products, such as E-CDS, E-WDG, E-DDG, or E-DDGS have at least about or about 45, 46, 47, 48, 49, 50, 51, 52, 53, 54, 55, 56, 57, 58, 59, 60, 61, 62, 63, 64, 65, 66, 67, 68, 69, or 70% crude protein on a dry weight basis, or between any two of these values. Crude protein represents the total dietary nitrogen (N) in the diet, which includes not only true protein but also non-protein nitrogen (e.g., urea and ammonia, but not nitrate). The protein content can also be measured as the weight percent of amino acids in the enhanced co-product. In some embodiments, an enhanced co-product has a total amino acid content of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60% on a dry weight basis, or between any two of these values. In some embodiments, an enhanced co-product has a total amino acid content of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60% by weight of the co-product.

Some embodiments of enhanced co-products have a lower percentage of fat than conventional co-products. In some embodiments, the enhanced co-products have at most about or about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0% fat on a dry weight basis, or between any two of these values.

Some embodiments of enhanced co-products have a reduced fiber content due to the fiber in the feedstocks being broken down into fermentable sugars in the methods disclosed herein. In some embodiments, the enhanced co-products have a fiber content that is at most about or is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% on a dry weight basis, or is between any two of these values. As used herein, the fiber content refers to NDF fiber content, which includes hemicellulose, cellulose, and lignin.

In some embodiments the enhanced co-products have a starch content that is at most about or about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0% on a dry weight basis or is between any two of those values.

In some embodiments, E-DDG or E-DDGS disclosed herein has a moisture content of at least about, at most about, or about 2, 3, 4, 5, 6, 7, 8, 9, 10, 11, 12, 13, 14, 15, 16, 17, 18, 19, 20, 21, 22, 23, 24, or 25%, or between any two of these values.

In some embodiments, the enhanced co-products have an ash content that is at most about or about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% on a dry weight basis, or is between any two of these values.

In some embodiments, the enhanced thin stillage produced according to the methods disclosed herein has a moisture content of 75, 76, 77, 78, 79, 80, 81, 82, 83, 84, 85, 86, 87, 88, 89, 90, 91, 92, 93, 94, or 95%, or between any two of these values. In some embodiments, the enhanced thin stillage has a crude protein content of at least about, at most about, or about 45, 46, 47, 48, 49, 50, 51, 52, 53, 54, 55, 56, 57, 58, 59, 60, 61, 62, 63, 64, 65, 66, 67, 68, 69, or 70% on a dry weight basis, or between any two of these values. The enhanced thin stillage may be dried to produce enhanced syrup having a moisture content of at least about, at most about, or about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75%, or between any two of these values. In some embodiments, the enhanced syrup has a crude protein content of at least about, at most about, or about 45, 46, 47, 48, 49, 50, 51, 52, 53, 54, 55, 56, 57, 58, 59, 60, 61, 62, 63, 64, 65, 66, 67, 68, 69, or 70% on a dry weight basis, or between any two of these values.

Embodiments of the enhanced co-products disclosed herein can have any combination of the properties described above. That is, the enhanced co-products can have any combination of two or more of the above-listed values for protein content, amino acid content, fat content, fiber content, starch content, moisture content, and/or ash content.

EXAMPLES

The disclosed compositions and methods will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Procedure for Production of Ethanol and Co-Products

The inventors performed several production runs to process wet cake feedstocks (with or without added thin stillage or syrup) to varying degrees. The general process of these runs included pre-treatment of the feedstock, enzymatic hydrolysis, fermentation, distillation, liquid-solid separation, and drying. These processes were performed in an existing biofuel plant. The features of the biofuel plant and the general procedures for processing biomass are as follows: Biomass (i.e., corn fiber-containing feedstock such as wet cake or a mixture of wet cake and thin stillage) is placed in a biomass hopper and transferred using a transfer screw into an ATM (atmospheric) steam bin, which has a bottom-mounted agitator that feeds the biomass into a plug-screw feeder (PSF). The PSF consists of a biomass inlet, tapered compression zone, screens coupled with a pressate outlet and chip outlet at the discharge into a twin-screw impregnator. The sudden expansion of biomass upon entry into the impregnator allows the chemicals (i.e., HESA cooking solution) to penetrate the biomass homogeneously. The highly compressed biomass is discharged into the impregnator via a blow-back piston (or dampener). In case the plug integrity is compromised, the blow-back dampener acts as a primary barrier preventing $SO_2$ laden vapors from being blown back from the high pressure digester back into the ATM bin. The fully impregnated biomass is elevated above the level of the liquid by counter-rotating twin screws and dropped into a digester. The digester has a conical profile to de-stress the solids as they build level from the bottom. The digest has a nuclear (gamma) level transmitter to monitor level and is mounted with temperature transmitters and controllers. The temperature in the digester is adjusted using steam. The digester has a spike-mounted bottom agitator and fully submerged transfer screw coupled to a cold-blow discharger. The cold-blow discharger has a hollow paddle coupled with a helical string mixer. The cold-blow discharge is coupled to a primary blow tank, which is close-coupled to a blow valve.

During the start-up, a plug is established in the PSF using the biomass. The dry-biomass feed rate is established a priori by calibrating the amount fed into an open digester by feeding a tote or two of the biomass. 50# Saturated steam is used to heat the digester until the typical target temperature is achieved. The bottom of the digester up to the cold-blow discharge in this process is filled with condensate, which is moved to the primary blow tank as needed. Once the target temperature in the digester is achieved, HESA and water are introduced, followed by the biomass (by running the transfer screw as needed to maintain a sufficient level in the ATM-bin and running the PSF) in proportions to provide the target liquid-to-biomass ratio (referred to as the L/W ratio (Liquor-to-Wood) or total solids concentration (TS %)). The biomass is filled up to a level to achieve the necessary residence time in the continuous-flow digester and maintained at that level. The bottom agitator in the digester is started ~10 minutes before the target residence time level is achieved. It was not necessary to run the discharge screw to move the cooked pulp into the cold-blow discharger. After the target residence time elapses, the blow-valve is opened to blow the pretreated pulp into the blow tank. Since the blow valve is oversized for the pre-treated feed consistency there is a small window (typically 5-10% of the valve opening) where a stable level in the digester can be maintained. Hence, the blow-out is essentially pulsed either automatically or manually.

Once blow-out of the pretreated pulp is started, an acid recovery system is brought online to the necessary temperature by heating the blow tank contents that are recirculated using a bottom PC (progressive-cavity) pump as set by the speed of the pump to achieve the target recirculation rate. 50# steam is used to heat this recirculation stream indirectly using a spiral exchanger. The recirculation loop pressure is regulated using a back-pressure control valve, which is positioned in the line directed back to the blow tank such that the stream gets to flash the acid once again in the blow tank. Note that the return nozzle (an open pipe in this case) is tangentially oriented. The blow tank level transmitter coupled with the PC pump directs a portion of the blown pulp into a secondary flash tank through a control valve, which is positioned in the recirculation line directed to the flash tank and gives another opportunity to flash the acid components in the secondary flash tank. The PC pump at the bottom of the flash tank, which is coupled with the flash tank level transmitter, is used to discharge the pretreated pulp (lean in acid) into a slop tank until steady state is achieved. As the PC pump is oversized, the flash tank level control was operated ON/OFF. The bottom of the flash tank is directed to slop tank for 2 hours and then collected in a day tank as representative pretreated material (lean-in-acid). The day tank is equipped to be able to neutralize the pretreated material to adjust pH as necessary for enzymatic hydrolysis using aqueous ammonia. Both the blow tank and the flash tank have side-mounted agitators at the bottom to avoid settling of solids.

The flashed vapors from the blow tank are directed via a vent manager system to the caustic scrubber coupled with an educator and a circulation system. The recovered acid components are captured as their salt in the scrubber (sodium hydroxyethane sulfonate).

Enzymatic hydrolysis and fermentation were performed in a swing tank having a nominal working volume of 2,200 gal. A beer column and rectification column were used to stage recovery of ethanol from fermentation broth, leaving behind enhanced whole stillage. A Sharples decanter centrifuge is coupled to the bottom of the beer column to perform solid-liquid separation of the enhanced whole stillage to make enhanced thin stillage and enhanced wet cake. A vacuum MVR (mechanical vapor compression) Evaporator was used to make enhanced syrup from the enhanced thin stillage.

Biomass feedstock (wet cake and thin stillage) were acquired from a dry mill corn ethanol plant. Wet cake was stored under refrigeration, and thin stillage was stored at 65 to 71° C.

The specific conditions for individual processing runs are described in the further Examples below. Except as indicated otherwise, the procedures for the subsequent Examples were carried out on the equipment and following the procedures described above in this Example 1.

Example 2

Pretreatment of Wet Cake Feed

Run 110: Wet cake was pretreated according to the process described in Example 1. The wet cake was impregnated with HESA solution and pretreatment was carried out in the digester at a temperature of 135±1° C. and a pressure of 50-70 psig, with a retention time of 60-75 min. The concentration of HESA in the digester was maintained at ~3%. The total solids percentage in the wet cake feed was between 35 and 38%, and the total solids percentages in the pretreated feed in the blow tank and flash tank were between 16 and 20%.

Example 3

Pretreatment of Wet Cake Feed, Enzymatic Hydrolysis, and Fermentation

Run 111: The same wet cake feed as used in Run 110 was pretreated under the conditions set forth above for Run 110. A portion of the pretreated wet cake was collected and used for enzymatic hydrolysis and fermentation. Two 28 L reactors were filled with 22.5 kg of the pretreated slurry. The temperature was increased to 52° C., and the pH was adjusted to 5.3 using 730-745 g of 14% ammonia. Lactrol was then added, along with 5% (20.16 g) of CTec3 HS enzyme, to each 28 L reactor. After 3 hours, some liquefaction was observable. The temperature was maintained at 52±1° C. for 72 hours (with the exception of 2 hours during which the temperature control malfunctioned, and the temperature ranged from 48.5 to 55.6° C. (which did not affect enzyme stability)), and the pH was maintained at 5.3. Fermentation was then performed by reducing the temperature set point to 32±1° C., adjusting the pH set point to 5.8±0.2, and inoculating the hydrolysate with yeast. Fermentation continued for 48 hours, during which the temperature and pH were maintained at the set points. The fermentation broth was then heated to 70° C. for 30 minutes to kill the yeast.

Figure 2:
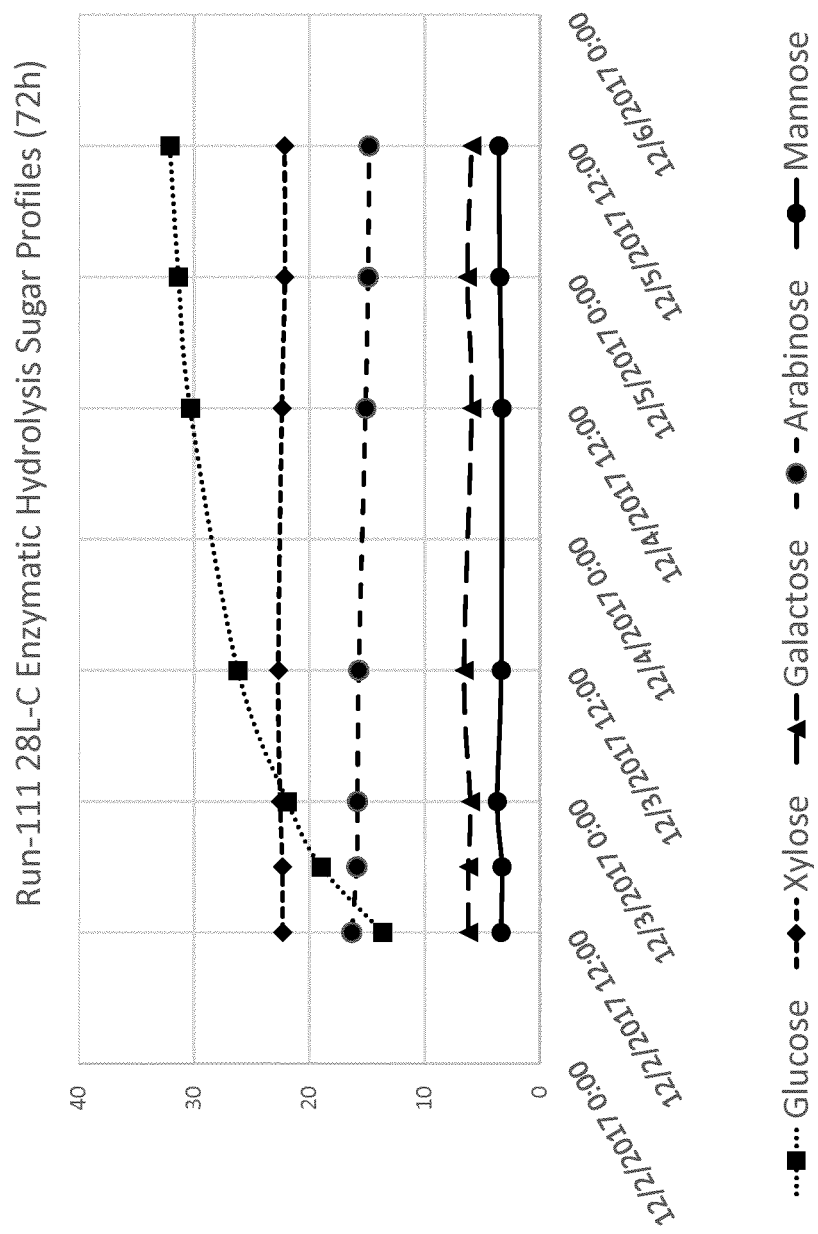
FIG. 2 shows the concentration (g/L) of the indicated sugars during enzymatic hydrolysis of pretreated feedstock (Run 111).
Figure 3:
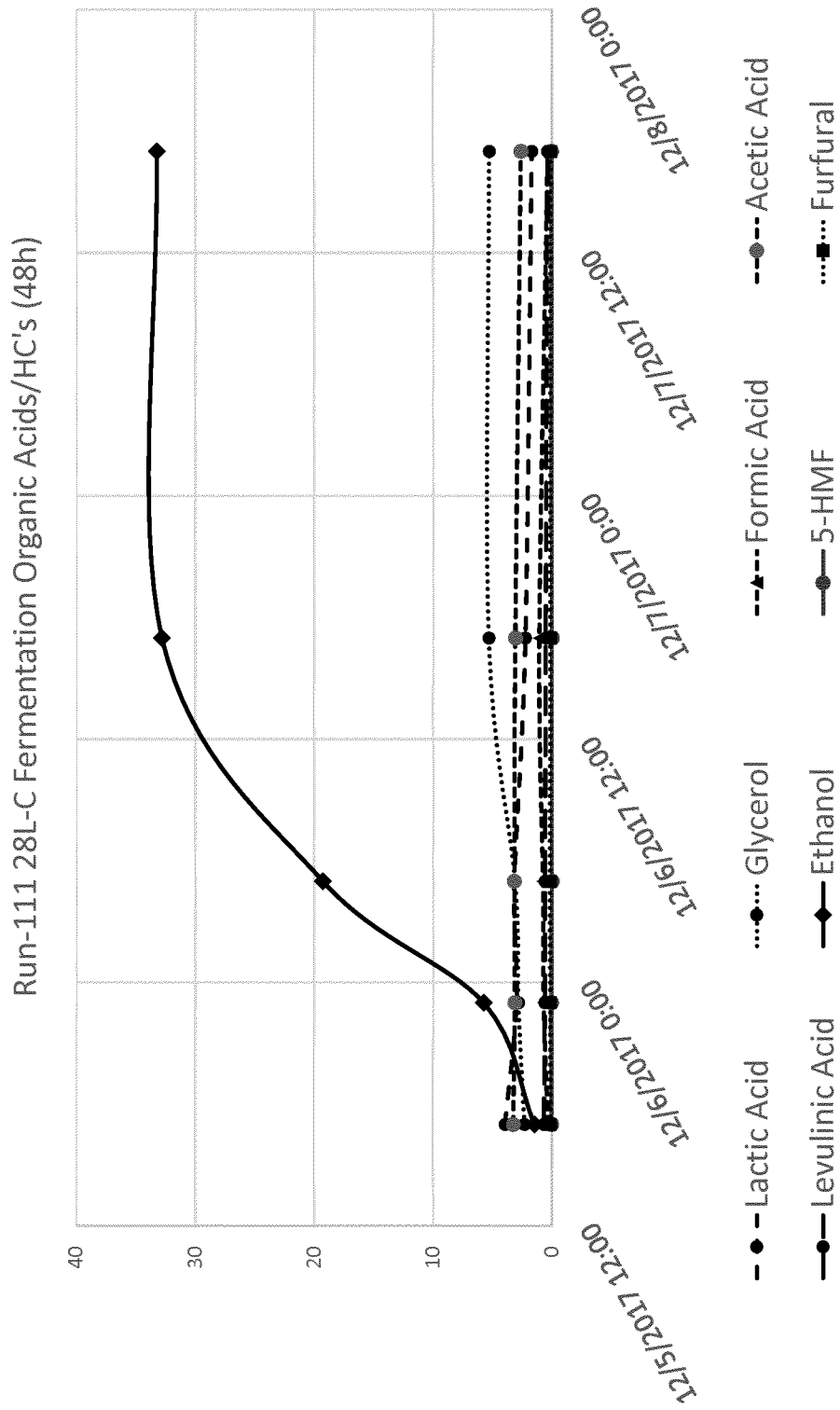
FIG. 3 shows the concentration of the indicated molecules (g/L) during fermentation (Run 111).
Figure 4:
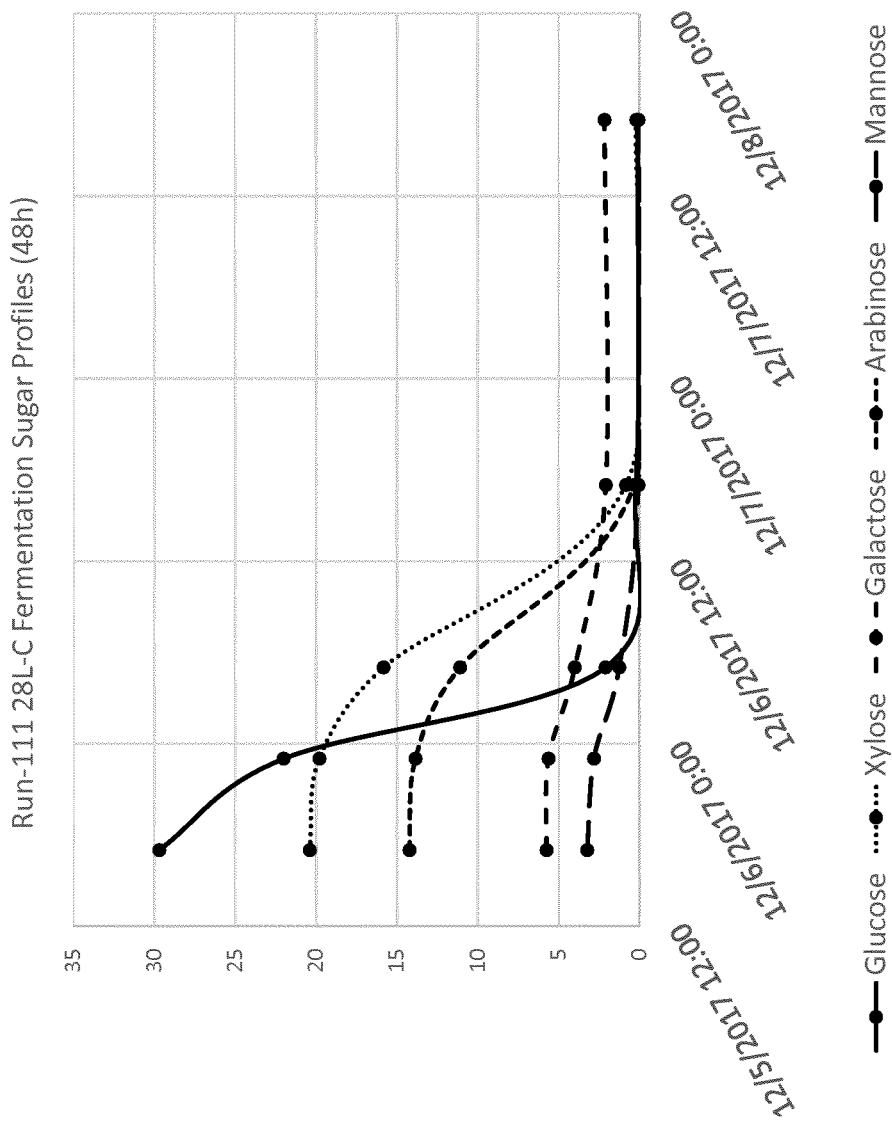
FIG. 4 shows the concentration (g/L) of the indicated sugars during fermentation (Run 111).

FIG. 2 shows that during hydrolysis of the pretreated wet cake in Run 111, the glucose concentration increased from about 12 g/L to about 32 g/L. FIG. 3 shows that during fermentation, the Ethanol concentration increased to about 32 g/L. FIG. 4 shows that the glucose, xylose, arabinose, and mannose present in the hydrolysate were substantially entirely consumed during fermentation.

Example 4

Pretreatment of Wet Cake Feed

Run 112: The same wet cake feed as used in Run 110 (Example 2) was pretreated under the conditions set forth for Run 110 above, except that the total concentration of HESA in the pretreated feed was between 1 and 1.4 wt % in the blow tank and between 0.6 and 0.9 wt % in the flash tank and the total solids percentages in the pretreated feed in the blow tank and flash tank were between 20 and 26%.

Example 5

Large-Scale Hydrolysis, Fermentation, and Production of Enhanced Co-Products from Pretreated Wet Cake Run 113: Pretreated wet cake slurry from Runs 110, 111, and 112 (~400 to 450 gal from each, for a total of ~1300 gal) was pooled into a 2000 gallon swing tank. The swing tank was set to maintain the temperature at 53±2° C. and the pH was set to be maintained at 5.3±0.2 by addition of 14.5% $NH_4OH$ as needed throughout the enzymatic hydrolysis step. Approximately 35 gal of 14.5% $NH_4OH$ was required to initially increase the pH to 5.3. Lactrol was added, followed by 5% (5.553 kg) of an enzyme cocktail including cellulase and hemicellulase activity, added gradually over the course of 75 minutes. Enzymatic hydrolysis continued under the same conditions for 72 hours.

A *Saccharomyces cerevisiae* yeast culture for fermentation was prepared by combining 400 L of sterilized YPD growth medium (10 g/L yeast extract, 20 g/L peptone, 50 g/L glucose, and 10 g/L xylose), 5 mg/L Lactrol, and 1 kg stabilized liquid yeast and incubating with an aeration rate of 0.2 vvm and 100 rpm agitation in a reactor for approximately 15 hours.

The wet cake hydrolysate in the swing tank was adjusted to pH 5.8 using $NH_4OH$ and cooled to 32° C., and the 400 L of yeast culture from the propagator was added to the swing tank. Fermentation continued with the temperature maintained at 32±1° C. and pH maintained at 5.8 for 40 hours. The fermentation broth (beer) was transferred to a distillation column and heated to 70° C. for 30 minutes for yeast kill. After distillation, 168 lbs of ~80% ethanol was collected, and 1300 gal of enhanced whole stillage was collected. The enhanced whole stillage was run through a Sharples centrifuge, which did not achieve good liquid-solid separation. The centrate was left overnight, after which DCO had separated as a layer on top of the enhanced whole stillage ("E-whole stillage"). The DCO was skimmed off, and the remaining enhanced whole stillage was run through a Flottweg decanter centrifuge run at 4000 rpm (9% torque). The enhanced whole stillage was 8-10% TS when fed into the centrifuge, and the exiting enhanced wet cake (enhanced wet distiller's grains, or "E-wet cake") was measured at 28.2% TS. 1 Gallon of this enhanced wet cake was air-dried to produce enhanced dried distiller's grains (E-DDG). The enhanced thin stillage from the Flottweg was sent to the MVR evaporated and concentrated 4× to make enhanced syrup ("E-syrup").

Figure 5:
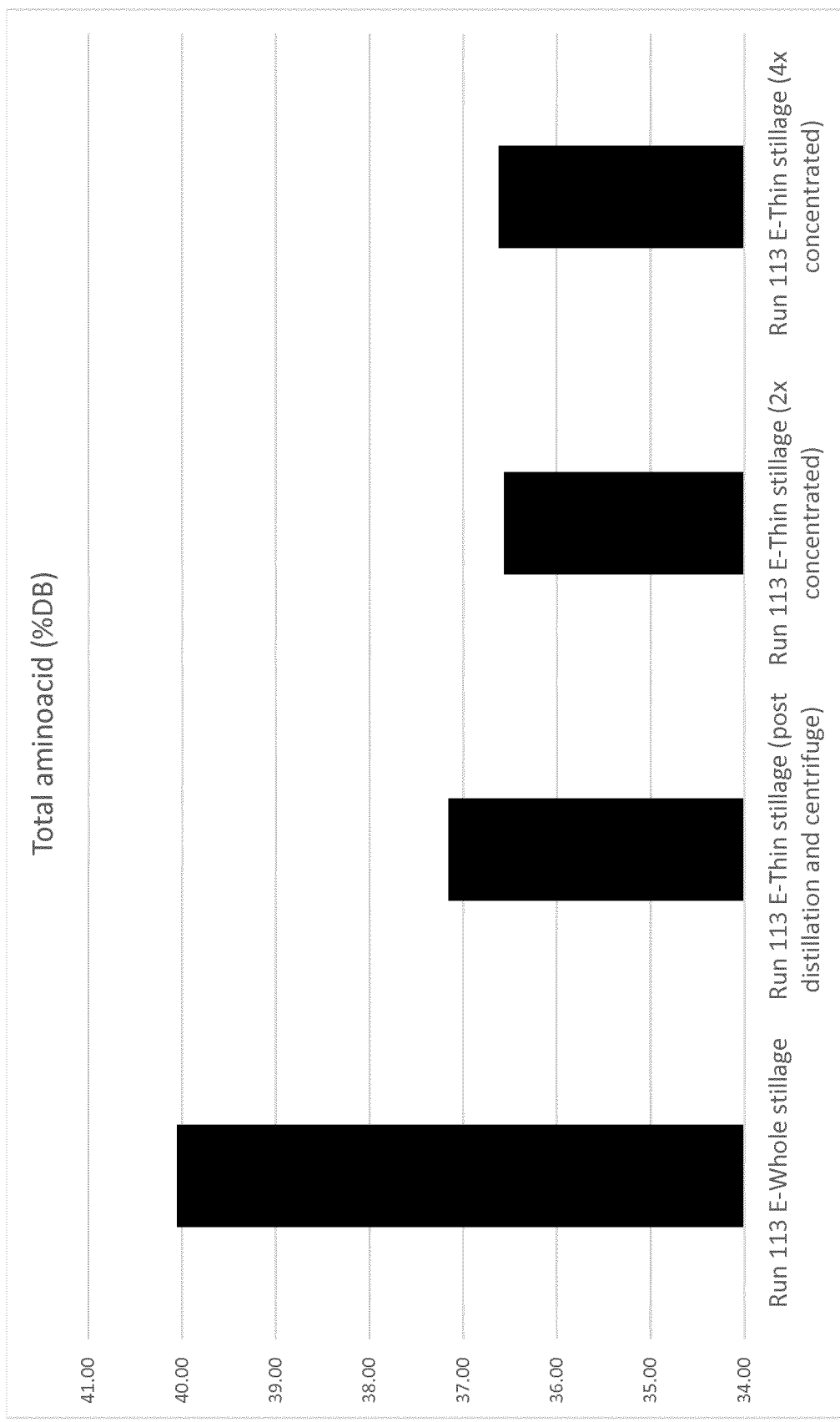
FIG. 5 shows the total amino acid concentration on a dry weight basis for the indicated co-products of an ethanol production process (Run 113).
Figure 6:
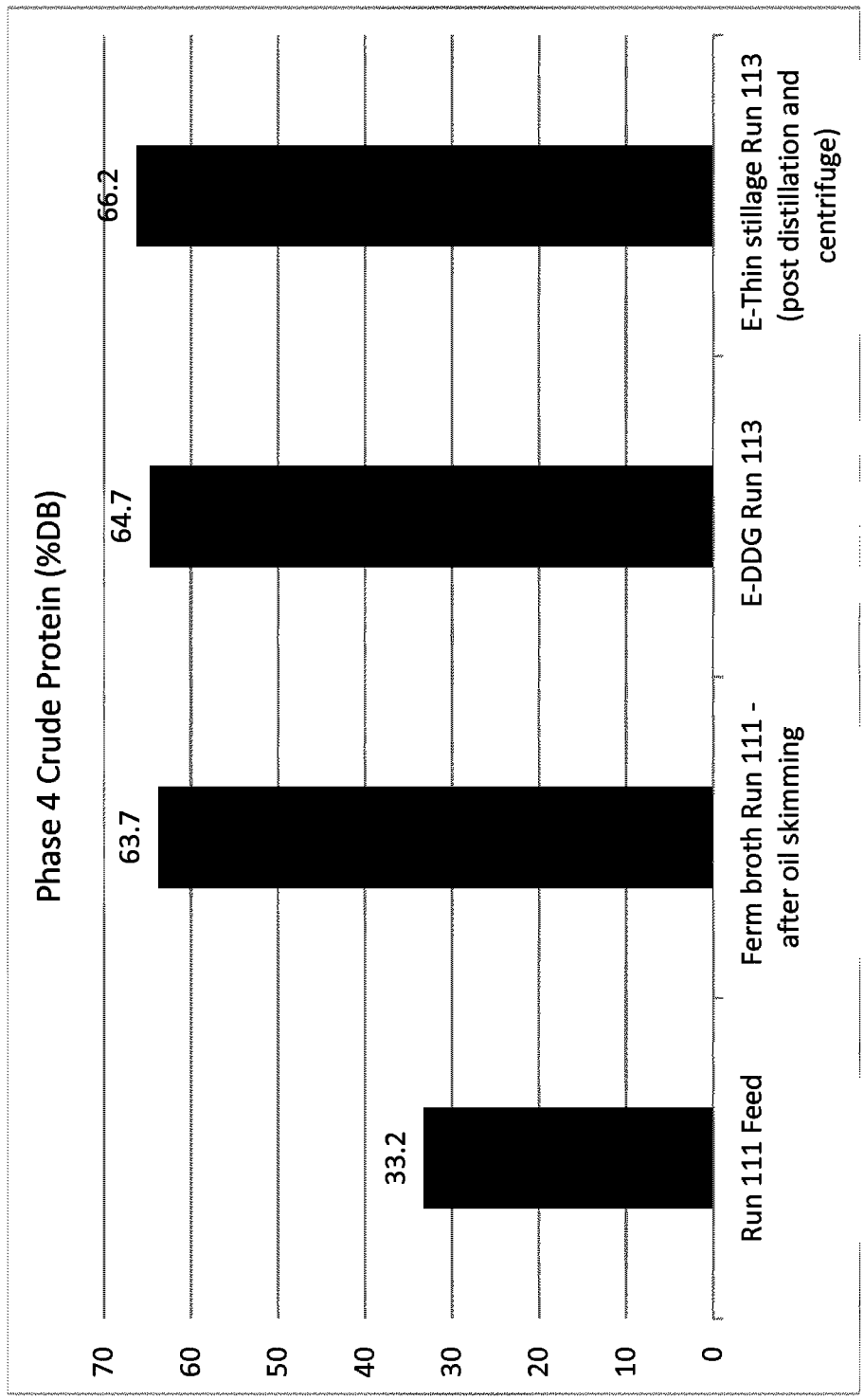
FIG. 6 shows the crude protein content on a dry weight basis for the indicated samples (Runs 111 and 113).
Figure 7:
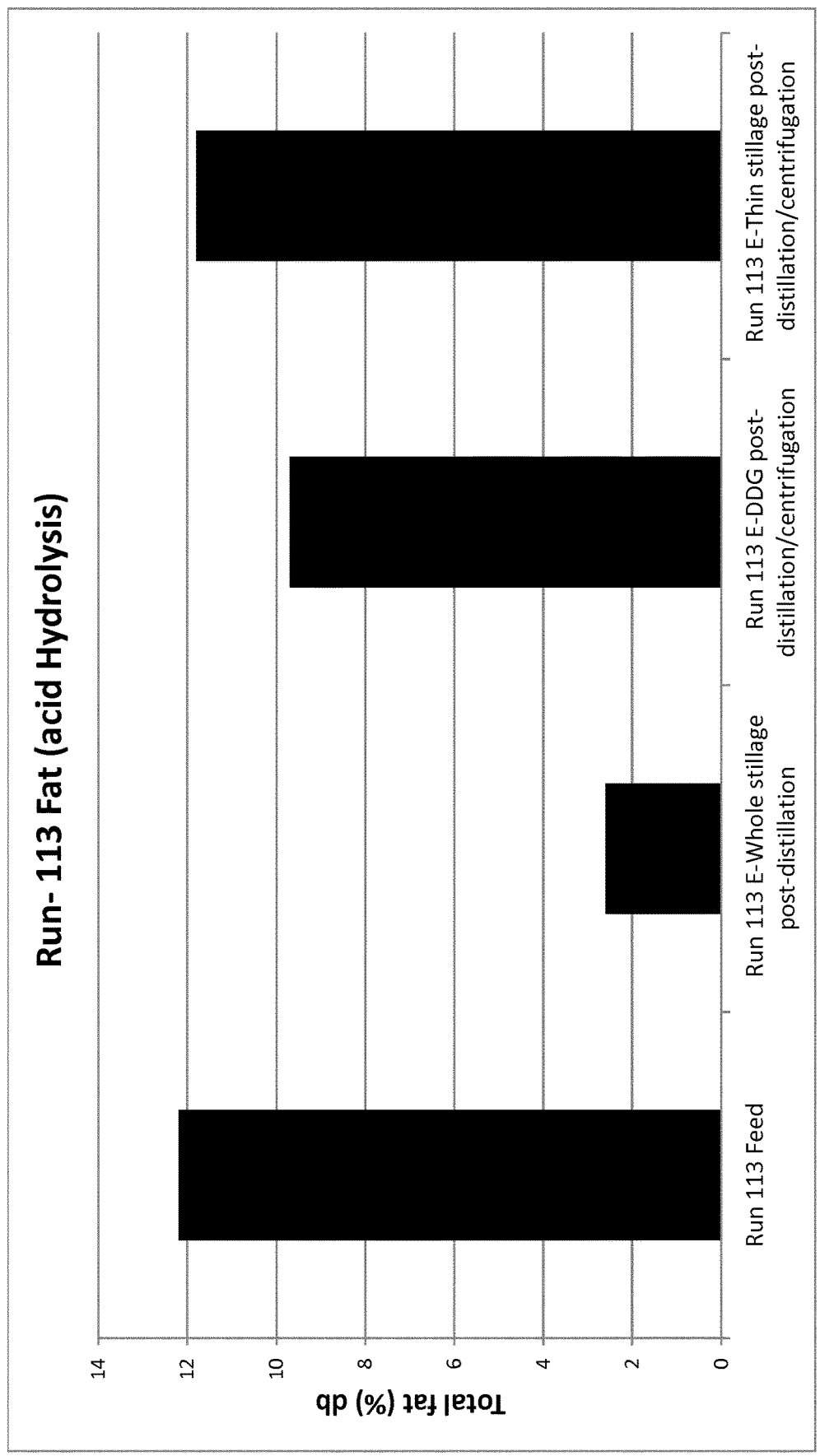
FIG. 7 shows the fat content on a dry weight basis for the indicated co-products of an ethanol production process (Run 113).

FIG. 5 shows the total amino acid content of the indicated samples from Run 113 on a dry weight basis. FIG. 6 shows the crude protein content of the indicated samples from Run 113 (including the wet cake feed from Run 111) on a dry weight basis. The crude protein content of a sample represents the total dietary nitrogen (N) in the diet, which includes not only true protein but also non-protein nitrogen (e.g., urea and ammonia, but not nitrate). FIG. 7 shows the total fat content on a dry weight basis of the indicated samples from Run 113, as measured by acid hydrolysis. Table 1 below sets forth properties of various samples of feed and co-products from Run 113.

TABLE 1

Properties of Feed and Co-products for Run 113

| Properties | Samples | | | | | | |
|---|---|---|---|---|---|---|---|
| | A | B | C | D | E | F | G |
| Moisture (wt %) | 62.4 | 90.0 | 33.6 | 89.3 | 89.2 | 13 | 57.3 |
| Crude protein (% DM) | 33.2 | 66.2 | 64.7 | 68.9 | 62.3 | 61 | 60.2 |
| Fiber - NDF (% DM) | 35.6 | 3.9 | 9.9 | 4.3 | 2.5 | 12.6 | 6.5 |
| Crude fiber (% DM) | 10.9 | 6.2 | 7.1 | 4.7 | 1 | 7.6 | 5.2 |
| Fat (% DM) | 12.6 | 2.7 | 6.5 | 2.6 | 11.8 | 9.66 | 13.3 |
| Ash (% DM) | 3.1 | 3.95 | 2.35 | 5.84 | 4.95 | 1.62 | 4.19 |
| Starch (% DM) | 1.6 | 0.1 | 0.8 | 0.1 | 0.1 | 0.1 | 0.1 |

A: Wet cake feed used for Runs 110, 111, 112, 113, and 116
B: Run 113 E-Thin stillage made by centrifuging sample of fermentation broth before distillation
C: Run 113 E-DDG made by centrifuging and drying sample of fermentation broth before distillation
D: Run 113 E-Whole stillage
E: Run 113 E-Thin stillage made by centrifuging E-whole stillage (after distillation)
F: Run 113 E-DDG made by centrifuging and drying E-whole stillage (after distillation)
G: Run 113 E-Syrup (4x concentrated E-thin stillage)
% DM: weight percent on a dry weight basis Example 6

Production of Ethanol from Wet Cake Mixed with Thin Stillage

Run 116: Wet cake (39% TS) from a dry mill corn ethanol plant was impregnated with HESA solution as it was fed into the digester. Thin stillage from the same corn ethanol plant was added to the digester as well. The mixed feed in the digester had 22% TS and 2.9 wt % HESA. Pretreatment was carried out in the digester at a temperature of 135±1° C. and a pressure of 35-50 psig, with a retention time of 60 min. Total solids percentages of the pretreated feed in the blow tank and flash tank were ~21%. A portion of the pretreated wet cake was collected and used for enzymatic hydrolysis and fermentation. Two 28 L reactors were filled with 22.5 kg of cooled, pretreated slurry. The temperature was increased to 52° C., and the pH was adjusted to 5.3 using 14.5% NH$_4$OH. Lactrol was then added, along with 5% (20.16 g) of CTec3 HS enzyme, to each 28 L reactor. The temperature was maintained at 52±1° C. for 72 hours, and the pH was maintained at 5.3. Fermentation was then performed by reducing the temperature set point to 32±1° C., adjusting the pH set point to 5.8±0.2, and inoculating the hydrolysate with yeast. Fermentation continued for 48 hours, during which the temperature and pH were maintained at the set points. The fermentation broth was then heated to 70° C. for 30 minutes to kill the yeast.

Figure 8:
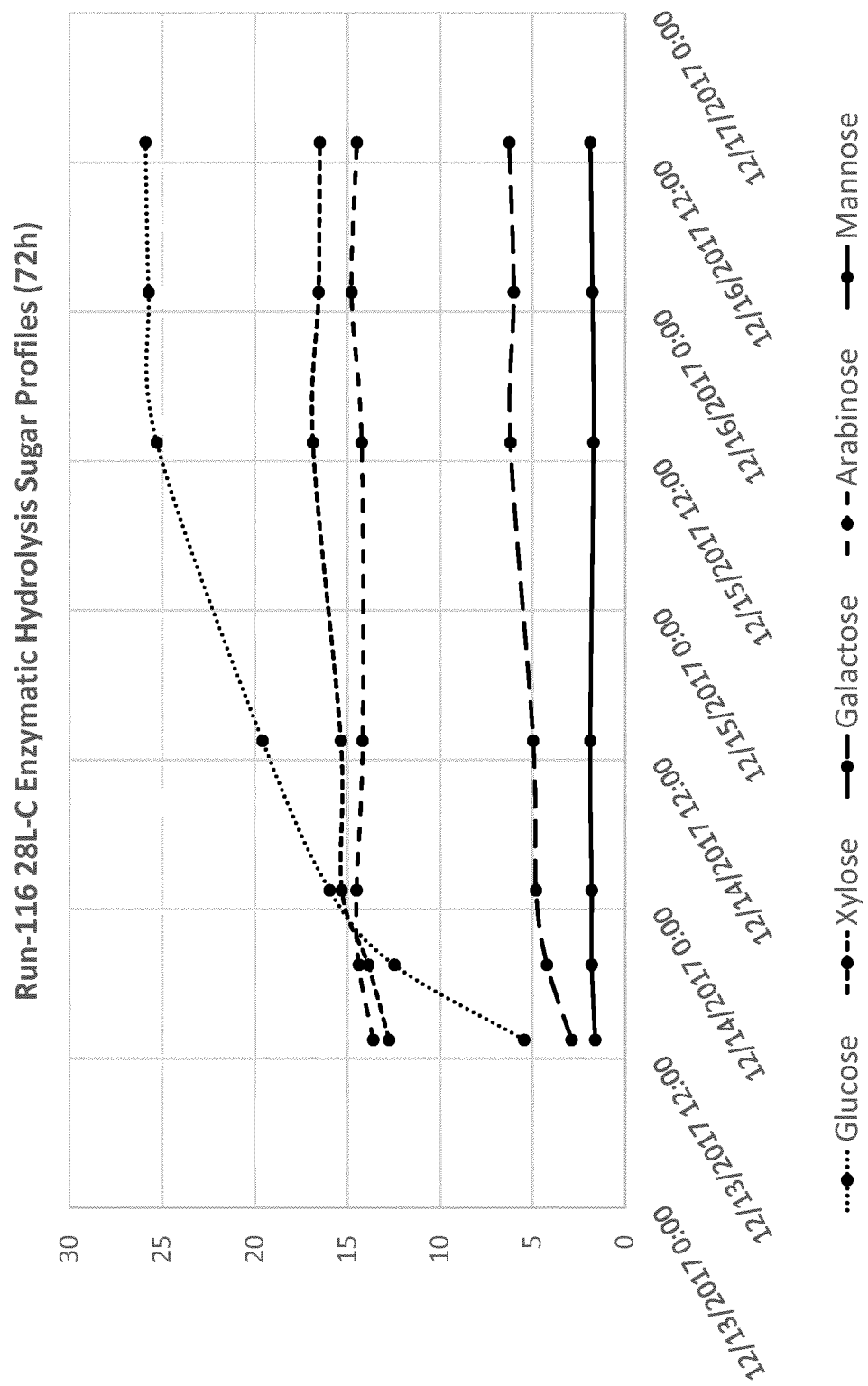
FIG. 8 shows the concentrations (g/L) of the indicated sugars during enzymatic hydrolysis of pretreated feedstock (Run 116).
Figure 9:
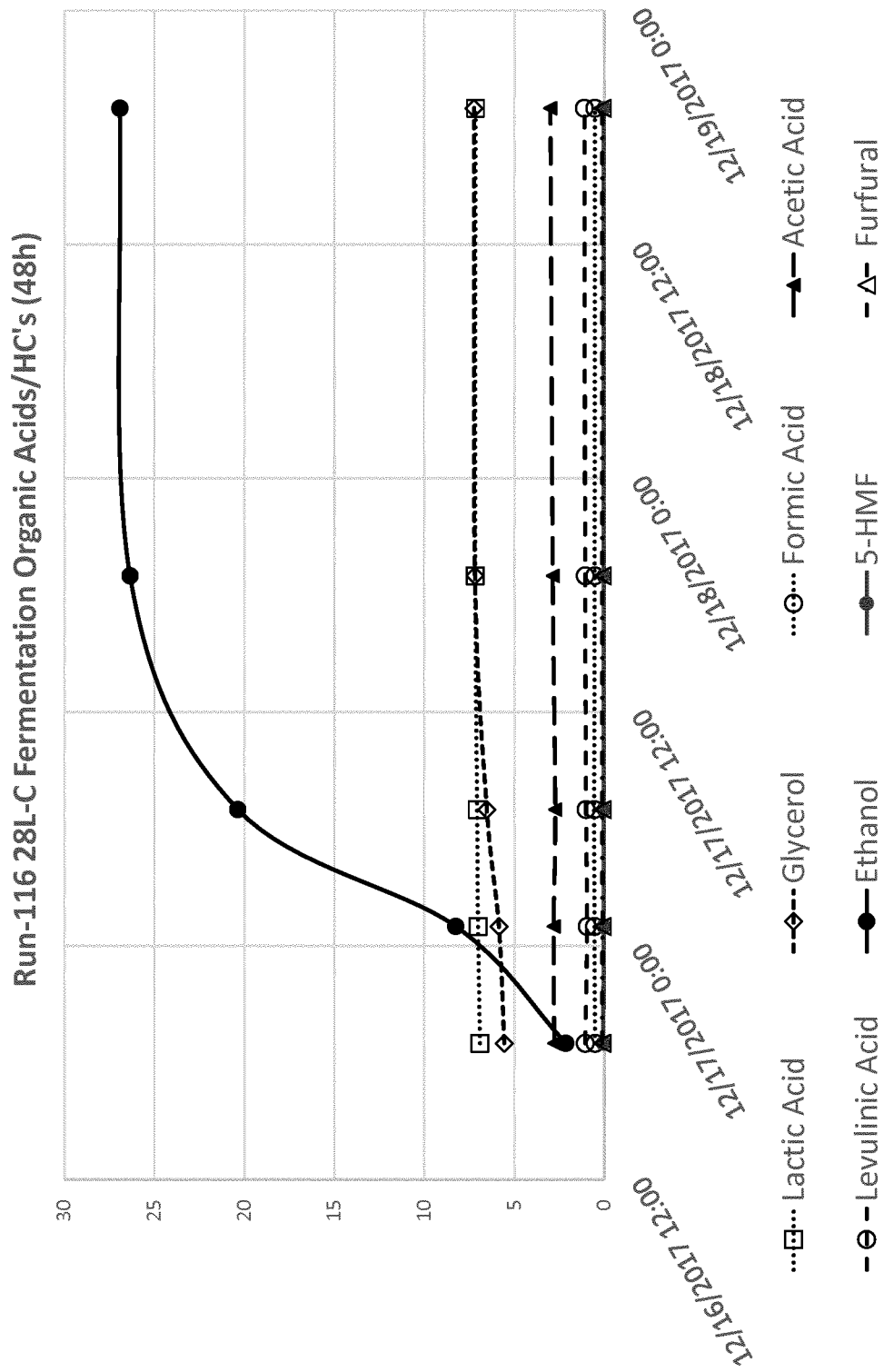
FIG. 9 shows the concentrations (g/L) of the indicated molecules during fermentation (Run 116).
Figure 10:
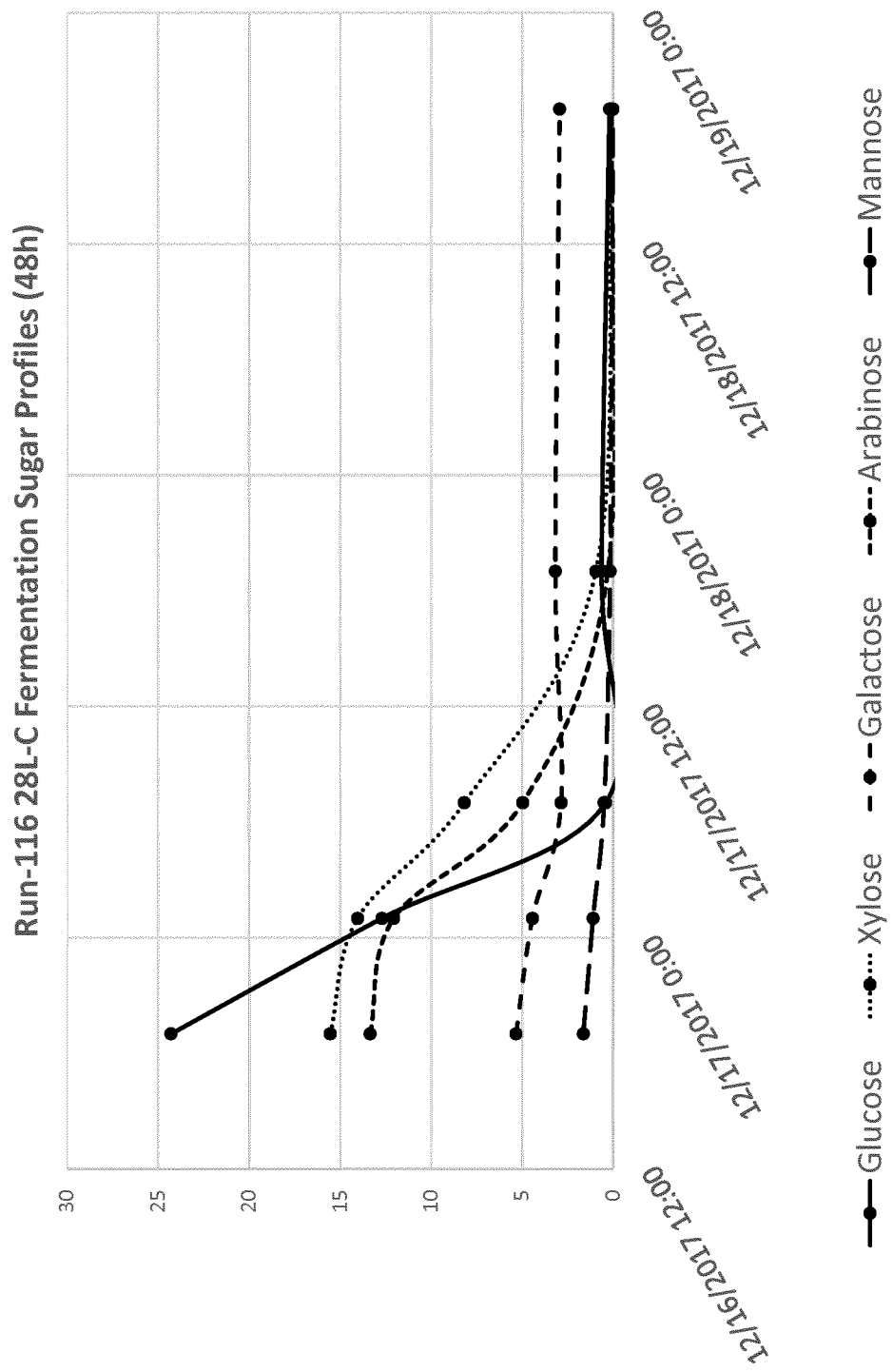
FIG. 10 shows the concentrations (g/L) of the indicated sugars during fermentation (Run 116).

FIG. 8 shows that during hydrolysis of the pretreated wet cake in Run 116, the glucose concentration increased from about 6 g/L to about 26 g/L. FIG. 9 shows that during fermentation, the Ethanol concentration increased to about 28 g/L. FIG. 10 shows that the glucose, xylose, arabinose, and mannose present in the hydrolysate were substantially entirely consumed during fermentation.

Example 7

Figure 11:
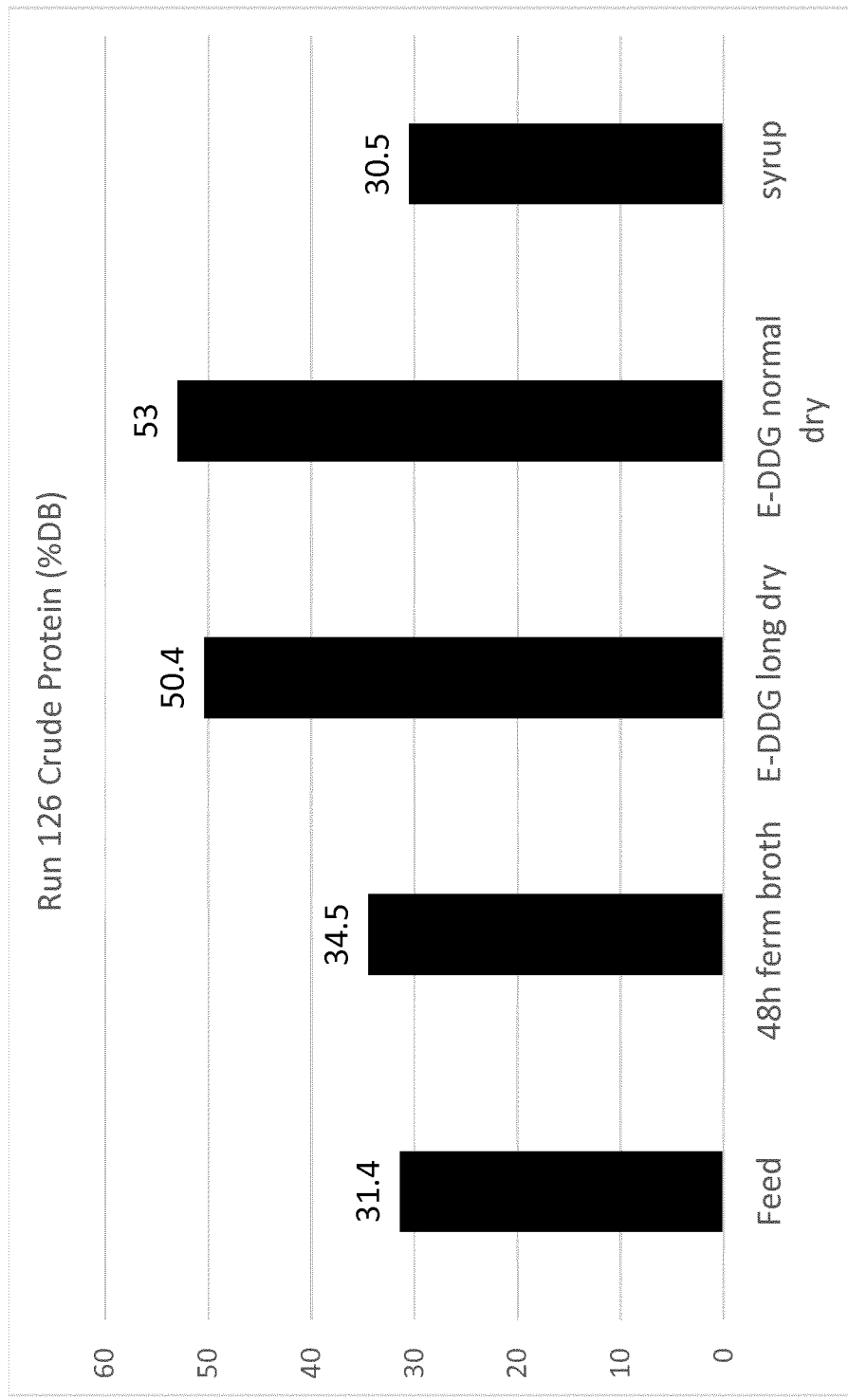
FIG. 11 shows the crude protein content on a dry weight basis for the indicated samples (Run 126).
Figure 12:
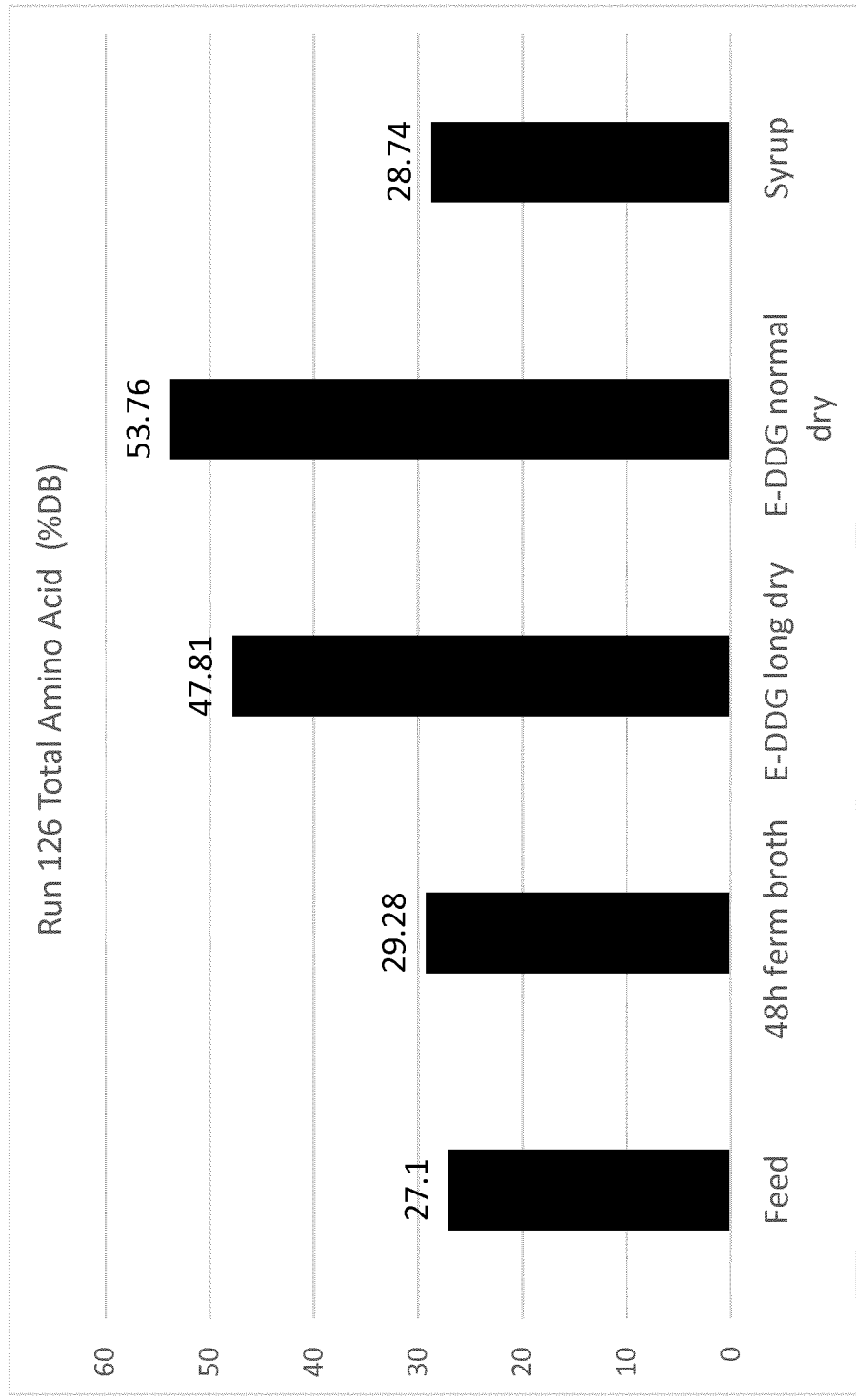
FIG. 12 shows the total amino acid content on a dry weight basis for the indicated samples (Run 126).
Figure 13:
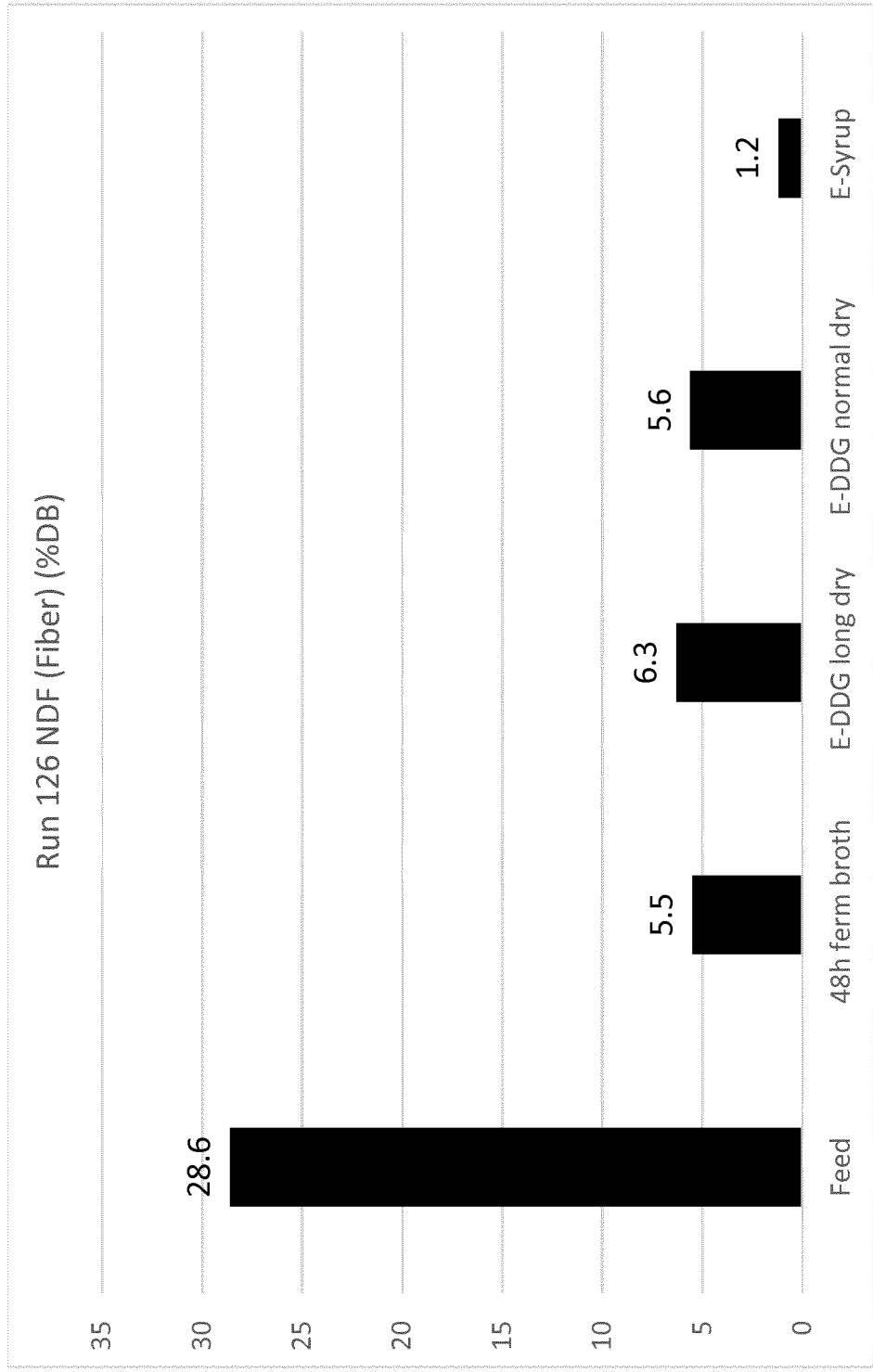
FIG. 13 shows the NDF fiber content on a dry weight basis for the indicated samples (Run 126).

Production of Ethanol and Enhanced Co-Products from Mixture of Wet Cake and Syrup Run 126: Ethanol was produced from a feed of wet cake mixed with condensed distiller's solubles (syrup) following the same protocol as Run 113. Two E-DDG samples were prepared from the enhanced wet cake post-centrifugation by oven drying: one "long-dry" sample and one "normal-dry" sample. FIG. 11 shows the crude protein content on a dry weight basis of the indicated samples from Run 126. FIG. 12 shows the total amino acid content on a dry weight basis of the indicated samples from Run 126. FIG. 13 shows the NDF content (hemicellulose, cellulose, and lignin) on a dry weight basis of the indicated samples from Run 126. Table 2 below sets forth properties of various samples from Run 126.

TABLE 2

Properties of Feed and Co-products for Run 126

| Properties | Samples | | | | | |
|---|---|---|---|---|---|---|
| | A | B | C | D | E | F |
| Moisture (wt %) | 51.6 | 79.3 | 84.4 | 86.6 | 4.7 | 11.6 |
| Crude protein (% DM) | 31.4 | 29.5 | 34.5 | 38.5 | 50.4 | 53 |
| Fiber - NDF (% DM) | 28.6 | 6.0 | 5.5 | 6.2 | 6.3 | 5.6 |
| Crude fiber (% DM) | 7.5 | 4.3 | 4.8 | 5.3 | 4.7 | 4.4 |
| Fat (% DM) (acid hydrolysis) | 12.2 | 9.37 | 6.99 | NT | 5.93 | 5.97 |
| Ash (% DM) | 5.78 | 7.51 | 12 | 18.9 | 16.8 | 10.4 |
| Starch (% DM) | 1.8 | 0.4 | 0.1 | 0.2 | 0.1 | 0.3 |

A: Run 126 Feed (wet cake mixed with condensed distiller's solubles)
B: Run 126 Pretreated slurry after pH adjustment
C: Run 126 Fermentation broth after 48 hours of fermentation
D: Run 126 E-Whole stillage
E: Run 126 E-DDG, long-dry sample
F: Run 126 E-DDG, normal-dry sample
NT: Not tested
% DM: weight percentage on a dry weight basis DCO was collected from whole stillage and analyzed to determine the fatty acid profile. The results are as follows, given in terms of weight percent: Total fatty acid: 90.8; C14:0 Myristic Acid: 0.07; C16:0 Palmitic Acid: 11.2; C16:1 Palmitoleic Acid: 0.14; C17:0 Heptadecanoic Acid: 0.06; C18:0 Stearic Acid: 1.71; C18:1w7 Vaccenic Acid: 0.69; C18:1w9 Oleic Acid: 24.9; C18:2w6 Linoleic Acid: 49.5; C18:3w3 Linolenic Acid: 1.13; C20:0 Arachidic Acid: 0.34; C20:1w9 Eicosenoic Acid: 0.21; C22:0 Behenic Acid: 0.11; C24:1 Nervonic Acid: n/a; C24:0 Lignoceric Acid: 0.15; Other Fatty Acids: 0.71.

The amino acid profile of the protein from the E-DDG normal-dry sample was determined to be as follows, given in terms of weight percent of the indicated amino acid in the E-DDG on a dry weight basis: cysteine: 0.8; methionine: 1.16; lysine: 1.41; alanine: 4.33; aspartic acid: 2.97; glutamic acid: 10.53; glycine: 2.15; isoleucine: 2.34; leucine: 7.57; proline: 4.48; threonine: 1.88; valine: 2.95; arginine: 1.98; histidine: 1.28; hydroxylysine: 0; hydroxyproline: 0; lanthionine: 0; ornithine: 0.05; phenylalanine: 2.8; serine: 2.62; taurine: 0.32; tyrosine: 1.75; tryptophan: 0.39; total amino acids: 53.8.

The above specification and examples provide a complete description of the implementation and structure of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the compositions, methods, and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary step or structure, and/or may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations unless such a limitation is explicitly recited in a given claim using the phrase(s) "means for" or "step for," respectively.

That which is claimed:

1. A method of processing fiber-containing co-products of an alcohol production process, the method comprising:
   (a) contacting polysaccharide fibers present in a mixture comprising one or more co-products of an alcohol production process with an α-hydroxysulfonic acid to hydrolyze at least a portion of the polysaccharide fibers, thereby generating fermentable sugars and releasing oil from the polysaccharide fibers, wherein the one or more co-products of an alcohol production process comprise one or more of the following:
      (i) wet distiller's grains;
      (ii) thin stillage;
      (iii) whole stillage; and
      (iv) gluten feed;
   (b) increasing the pH of the mixture by adding a base to the mixture;
   (c) contacting polysaccharide fibers in the mixture with enzymes to hydrolyze the polysaccharide fibers, thereby generating additional fermentable sugars and releasing further oil from the polysaccharide fibers, wherein the temperature of the mixture is between 50 and 55° C.;
   (d) incubating the mixture with yeast under anaerobic conditions to produce alcohol by fermenting fermentable sugars produced in steps (a) and (c), wherein the temperature of the mixture is between 25 and 35° C.;
   (e) distilling the mixture to remove alcohol from the mixture, thereby producing an alcohol-containing distillate and enhanced whole stillage;
   (f) removing released oil from the fermented mixture produced in step (d) and/or from the enhanced whole stillage produced in step (e);
   (g) separating the enhanced whole stillage to produce enhanced wet distiller's grains and enhanced thin stillage; and
   (h) drying the enhanced wet distiller's grains to remove moisture, thereby producing enhanced dried distiller's grains (E-DDG).

2. The method of claim 1, wherein the α-hydroxysulfonic acid is between 1 and 10% by weight of the mixture in step (b).

3. The method of claim 1, wherein the yeast is capable of fermenting five-carbon fermentable sugars.

4. The method of claim 1, further comprising:
   filtering the enhanced thin stillage produced in step (g) through one or more membranes to produce a protein-enriched retentate with a reduced sulfur content as compared to the enhanced thin stillage; or
   mixing the enhanced thin stillage produced in step (g) with an organic solvent to precipitate proteins in the enhanced thin stillage, separating the precipitate from the supernate, and mixing the precipitate with the enhanced wet distiller's grains produced in step (g) either before or during step (h).

5. The method of claim 1, wherein step (f) further comprises separating the oil from the fermented mixture using a gravity settler, allowing the fermented mixture to sit without agitation to allow the oil to separate from the fermented mixture, centrifuging the enhanced whole stillage to separate the oil from the enhanced whole stillage, allowing the enhanced whole stillage to sit without agitation to allow the oil to separate from the enhanced whole stillage, or a combination thereof.

6. The method of claim 1, wherein the weight of the oil removed in step (f) is at least 5% of the total weight of the enhanced whole stillage before removal of the oil.

7. The method of claim 1, wherein:
   during step (a), the mixture comprises wet distiller's grains, the concentration of α-hydroxysulfonic acid is between 2.5 and 3.5% by weight of the mixture, the temperature of the mixture is between 130 and 140° C., and step (a) continues for at least 50 minutes;
   step (b) comprises increasing the pH to between 5.0 and 5.5;
   during step (c), the concentration of enzymes is between 4 and 6% on a dry weight basis, and step (c) continues for at least 24 hours;
   step (d) continues for at least 24 hours;
   and the enhanced thin stillage produced in step (g) has a crude protein content of at least 45% on a dry weight basis.

8. The method of claim 7, further comprising drying the enhanced thin stillage produced in step (g) to produce an enhanced syrup having a moisture content of 50 to 75% by weight and adding the enhanced syrup to the enhanced wet distiller's grains before or during the drying of step (h).

9. The method of claim 7, wherein
   the drying of step (h) continues until the moisture content of the E-DDG is 5 to 15% by weight; and
   the E-DDG produced in step (h) has one or more of the following properties:
      a total protein content of at least 45% on a dry weight basis, preferably at least 65% on a dry weight basis;
      a total fat content of no more than 10% on a dry weight basis;
      a fiber content of less than 5% on a dry weight basis;
      a starch content of less than 1% on a dry weight basis; and
      an ash content of less than 2% on a dry weight basis.

10. A method of processing fiber-containing co-products of an alcohol production process, the method comprising:
   (a) contacting polysaccharide fibers present in a mixture comprising wet distiller's grains with α-hydroxyethane sulfonic acid at a concentration of 2.5 to 3.5% by weight of the mixture, at a temperature of 130 to 140° C., for a duration of at least 50 minutes to hydrolyze at least a portion of the polysaccharide fibers, thereby generating fermentable sugars and releasing oil from the polysaccharide fibers;
   (b) increasing the pH of the mixture to between 5.0 and 5.5 by adding a base to the mixture;
   (c) contacting polysaccharide fibers in the mixture with enzymes at a concentration of from 4 to 6% on a dry weight basis at a temperature between 50 and 55° C. to hydrolyze the polysaccharide fibers, thereby generating additional fermentable sugars and releasing further oil from the polysaccharide fibers;
   (d) incubating the mixture with yeast under anaerobic conditions for at least 24 hours to produce alcohol by fermenting fermentable sugars produced in steps (a) and (c), wherein the temperature of the mixture is between 25 and 35° C.;

(e) distilling the mixture to remove alcohol from the mixture, thereby producing an alcohol-containing distillate 5 and enhanced whole stillage;

(f) removing released oil from the fermented mixture produced in step (d) and/or from the enhanced whole stillage produced in step (e);

(g) separating the enhanced whole stillage to produce enhanced wet distiller's grains and enhanced thin stillage; and (h) drying the enhanced wet distiller's grains to reduce the moisture content to between 5 and 15%, thereby producing enhanced dried distiller's grains E-DDG).

11. The method of claim 10, wherein the G-DDG produced in step (h) has one or more of the following properties:

a total protein content of at least 45% on a dry weight basis;

a total fat content of no more than 10% on a dry weight basis;

a fiber content of less than 5% on a dry weight basis;

a starch content of less than 1% on a dry weight basis; and an ash content of less than 2% on a dry weight basis.

12. The method of claim 11, wherein wet distiller's grains are used as the feed for step (a) and wherein the total protein content of the E-DDG produced in step (h) is at least 55% on a dry weight basis.

\* \* \* \* \*